(12) United States Patent
Taylor et al.

(10) Patent No.: US 11,213,458 B2
(45) Date of Patent: Jan. 4, 2022

(54) SYSTEM AND METHOD FOR MONITORING INTAKE COMPLIANCE

(71) Applicant: Access Business Group International LLC, Ada, MI (US)

(72) Inventors: Joshua B. Taylor, Rockford, MI (US); Colin J. Moore, Grand Rapids, MI (US); Greg George Hillebrand, Whitehall, MI (US)

(73) Assignee: Access Business Group International LLC, Ada, MI (US)

( * ) Notice: Subject to any disclaimer, the term of this patent is extended or adjusted under 35 U.S.C. 154(b) by 0 days.

(21) Appl. No.: 17/112,291

(22) Filed: Dec. 4, 2020

(65) Prior Publication Data

US 2021/0085565 A1 Mar. 25, 2021

Related U.S. Application Data

(63) Continuation of application No. 15/925,884, filed on Mar. 20, 2018, now Pat. No. 10,874,591.

(Continued)

(51) Int. Cl.
*A61J 7/04* (2006.01)
*B65D 51/24* (2006.01)
(Continued)

(52) U.S. Cl.
CPC .......... *A61J 7/0418* (2015.05); *A61J 7/0436* (2015.05); *B65D 41/04* (2013.01); *B65D 51/24* (2013.01);
(Continued)

(58) Field of Classification Search
None
See application file for complete search history.

(56) References Cited

U.S. PATENT DOCUMENTS

| | | |
|---|---|---|
| 3,998,356 A | 12/1976 | Christensen |
| 4,911,327 A | 3/1990 | Shepherd et al. |

(Continued)

FOREIGN PATENT DOCUMENTS

| | | |
|---|---|---|
| CN | 102458344 | 5/2012 |
| DE | 91 14 688 | 3/1993 |

(Continued)

OTHER PUBLICATIONS

Sandler, J., "Pill Bottle Animation", retrieved from URL https://vimeo.com/20516252 on May 29, 2015.

(Continued)

*Primary Examiner* — Carlos Garcia
(74) *Attorney, Agent, or Firm* — Warner Norcross + Judd LLP

(57) ABSTRACT

A product interaction monitor includes sensors for measuring characteristics related to the product and/or product package or other type of container. The product interaction monitor can be installed in a container cap and used to monitor events associated with the container such as product usage. The product interaction monitor can utilize multiple sensor outputs to increase the accuracy of the detection of the events. The product interaction monitor can be used to estimate product inventory or product usage and communicate information regarding the product and/or product usage to a local display or a remote computer.

20 Claims, 20 Drawing Sheets

Related U.S. Application Data

(60) Provisional application No. 62/473,682, filed on Mar. 20, 2017.

(51) Int. Cl.
- *B65D 41/04* (2006.01)
- *G16H 20/10* (2018.01)
- *G08B 21/24* (2006.01)
- *G16H 20/13* (2018.01)
- *A61J 1/03* (2006.01)
- *A61J 1/14* (2006.01)

(52) U.S. Cl.
CPC .............. *G08B 21/24* (2013.01); *G16H 20/10* (2018.01); *G16H 20/13* (2018.01); *A61J 1/03* (2013.01); *A61J 1/1412* (2013.01); *A61J 7/0481* (2013.01); *A61J 2200/30* (2013.01); *A61J 2200/70* (2013.01); *A61J 2200/72* (2013.01)

(56) References Cited

U.S. PATENT DOCUMENTS

| | | | |
|---|---|---|---|
| 5,522,525 | A | 6/1996 | McLaughlin et al. |
| 6,216,910 | B1 | 4/2001 | Numerick |
| 6,805,259 | B2 | 10/2004 | Stevens et al. |
| 6,860,403 | B1 | 3/2005 | Mehrens et al. |
| 7,080,755 | B2 | 7/2006 | Handfield et al. |
| 7,100,797 | B2 | 9/2006 | Kahn et al. |
| 7,269,476 | B2 | 9/2007 | Ratnakar |
| 7,831,336 | B2 | 11/2010 | Gumpert |
| 7,873,435 | B2 | 1/2011 | Yuyama et al. |
| 7,988,016 | B2 | 8/2011 | Klein et al. |
| 8,326,455 | B2 | 12/2012 | Dunn |
| 9,218,458 | B2 | 12/2015 | Baarman et al. |
| 9,361,780 | B2 * | 6/2016 | Burke, Jr ............... G16H 20/13 |
| 9,597,261 | B2 | 3/2017 | Baarman et al. |
| 10,874,591 | B2 | 12/2020 | Taylor et al. |
| 2005/0151625 | A1 | 7/2005 | Lai |
| 2006/0006064 | A1 | 3/2006 | Udaka et al. |
| 2007/0108219 | A1 | 5/2007 | Handfield et al. |
| 2009/0301925 | A1 | 12/2009 | Alloro et al. |
| 2010/0314282 | A1 | 12/2010 | Bowers |
| 2011/0060457 | A1 | 3/2011 | De Vrught et al. |
| 2011/0217681 | A1 | 9/2011 | Krejcarek |
| 2011/0227734 | A1 | 9/2011 | Ortenzi et al. |
| 2011/0227735 | A1 | 9/2011 | Fawcett et al. |
| 2012/0187142 | A1 | 7/2012 | Flowers et al. |
| 2012/0259457 | A1 | 10/2012 | Handfield et al. |
| 2013/0110283 | A1 | 5/2013 | Baarman et al. |
| 2014/0188502 | A1 | 7/2014 | Defrank et al. |
| 2014/0266760 | A1 | 9/2014 | Burke, Jr. et al. |
| 2014/0305963 | A1 | 10/2014 | Zonana et al. |
| 2014/0335490 | A1 | 11/2014 | Baarman et al. |
| 2015/0257981 | A1 | 9/2015 | Arad et al. |
| 2015/0266654 | A1 | 9/2015 | Baarman et al. |
| 2016/0253477 | A1 | 9/2016 | Xu et al. |
| 2018/0319570 | A1 | 11/2018 | Baarman et al. |

FOREIGN PATENT DOCUMENTS

| | | |
|---|---|---|
| EP | 0 924 655 | 6/1999 |
| EP | 1 813 249 | 8/2007 |
| FR | 2 641 764 | 7/1990 |
| JP | H06-511183 | 12/1994 |
| JP | H10-201827 | 8/1998 |
| JP | H11-280317 | 10/1999 |
| JP | 2002-165866 | 6/2002 |
| JP | 2004-148036 | 5/2004 |
| JP | 2005-40459 | 2/2005 |
| JP | 2006-092197 | 4/2006 |
| JP | 2009-243098 | 10/2009 |
| JP | 2010-170504 | 8/2010 |
| JP | 2011-031006 | 2/2011 |
| JP | 2011-072749 | 4/2011 |
| WO | 94/04966 | 3/1994 |
| WO | 94/14682 | 7/1994 |
| WO | 96/17330 | 6/1996 |
| WO | 00/56264 | 9/2000 |
| WO | 01/94205 | 12/2001 |
| WO | 02/41825 | 5/2002 |
| WO | 2009/080309 | 7/2009 |
| WO | 2011/154018 | 12/2011 |
| WO | 2012/002609 | 1/2012 |

OTHER PUBLICATIONS

Brody, T., "Clinical Trials—Study Design, Endpoints and Biomarkers, Drug Safety, and FDA and ICH Guidelines", Chapter 8 Intent to Treat Analysis vs. Per Protocol Analysis, ISBN: 978-0-12-391911-3, pp. 143-164.

International Search Report and Written Opinion of the International Searching Authority for International Application No. PCT/US2012/034932 dated Oct. 10, 2012.

Invitation to Pay Additional Fees and Partial International Search Report for International Application No. PCT/US2015/021166, dated Jun. 10, 2015.

International Search Report and Written Opinion of the International Searching Authority for International Application No. PCT/US2015/021166 dated Sep. 4, 2015.

International Search Report and Written Opinion of the International Searching Authority for International Application No. PCT/US2018/023224 dated Jun. 6, 2018.

* cited by examiner

OPEN AND CLOSE EVENT

SYSTEM AND METHOD FOR MONITORING INTAKE COMPLIANCE

BACKGROUND OF THE INVENTION

One aspect of the present invention relates to monitoring consumable package activity. Another aspect of the invention relates to monitoring consumable inventory. Another aspect relates to monitoring user behavior characteristics. Another aspect relates to informing and providing reminders to assist users in maintaining usage compliance of consumables. Yet another aspect relates to simplifying reordering of consumables.

Many health and nutrition products such as dietary supplements, vitamins, skin care products and other medicaments need to be used according to the usage directions for optimum efficacy and safety. However, lack of compliance or adherence to usage directions is a common problem with consumers who may, for example, under-use or over-use a product. Compliance is also important in clinical trials. Clinical trials are frequently conducted to determine the product or drug's safety and efficacy or to generate product claims. During these clinical trials, subjects are asked to follow a specific protocol for using the product. Subject compliance to the protocol is essential for accurate determination of the test product's safety and efficacy.

For consumers at home, compliance relies primarily on a consumer's ability to remember to take the supplement or medicament according to directions. Compliance may be improved by using aids like pill boxes to help organize the medication or supplement on a daily, weekly or monthly basis. The user is also expected to remember to purchase replacement product and failure to do so can lead to a complete lack of compliance. In today's busy world, users have a lot of things happening in their lives and remembering to do something on a daily basis can easily be forgotten or avoided due to the hassle. The same goes for reordering to ensure timely delivery of new product and the prevention of gaps in compliance.

For clinical trials, compliance is frequently measured by the difference in the amount of product returned at follow-up to the amount provided at baseline. This can be the number of pills apparently taken or the weight of the product apparently consumed during the test period. However, it is unknown if the subject actually took the product or simply disposed of enough product so that it looked like it was used.

Systems and methods are needed to improve compliance both at home and in the clinic.

SUMMARY OF THE INVENTION

The present invention is directed to a product interaction monitor that includes one or more sensors and a power source. The monitor is installed in a consumable package or replaceable component for the consumable package, such as a lid or cap. The product interaction monitor can monitor activity, such as smart cap events or inventory information, which can be stored in memory and reported to a user. Smart cap events can include user behaviors, for example opening a cap, closing a cap, or pumping a pump dispenser.

In one embodiment, the product interaction monitor can be installed in a twist off cap for a consumable product package. Using a combination of sensor output from a gyroscope and an accelerometer, the product interaction monitor can accurately determine an opening event where the cap is removed from the product package and a closing event where the cap is secured to the product package. The accelerometer can be used to wake-up the gyroscope, which can be configured to determine the user is twisting off the cap. The product interaction monitor can distinguish twisting the cap from some other twisting activity by monitoring the gyroscope for a certain number of measurements above a predetermined threshold within a predetermined amount of time. Further, the opening event can be contingent on further sensor output, for example an opening event may not be logged until the product interaction monitor determines the user twisted off the cap and also set the cap down. Setting the cap down can be determined by the product interaction monitor by a certain accelerometer output for a predetermined duration within a timeout period after the user twist is detected. In alternative embodiments, the product interaction monitor can be installed in different types of caps for a consumable product package and can use a combination of sensor output to determine opening and closing events.

The opening and closing events can be used to estimate the product inventory and product freshness. For example, each opening event can be associated with a predetermined amount of inventory use based on the directed use of the product. The wireless communication system can communicate with a remote reordering system to automatically reorder product if the inventory dips below a certain threshold. As another example, each opening and closing event can be used to track the amount of time the product container is open, which can be used to assess and track product freshness.

In another embodiment, the product interaction monitor can be installed in a pump dispensing cap for a consumable product package. Using a combination of sensor output, for example from a capacitive sensor and an accelerometer, the product interaction monitor can accurately determine a pump event indicative of how much product is dispensed from the product package. Using combinations of thresholds and timings associated with the output of the capacitive touch sensor and the accelerometer, the product interaction monitor can count the number of pumps and the travel distance of the pump, which allows for tracking the amount of product dispensed.

The pump dispense events can be used to estimate the product inventory and product freshness. For example, the characteristics of each pump dispense event can be used to determine the amount of product dispensed. The wireless communication system can communicate with a remote reordering system to automatically reorder product if the inventory dips below a certain threshold.

Certain information can be conveyed to a user using various wireless communication technologies and displays, for example information can be communicated to a user's personal device for display there. Alternatively or additionally, information can be provided from the package itself, for example via a display system on the package itself or a speaker. For example, FIG. 16 illustrates a container 204 with a smart cap 1000 that includes an LED ring reminder 1602, an inventory display 1604, and a speaker 1606 for providing audible reminder alerts. This information can be utilized to inform the user and provide reminders to users for maintaining usage compliance as well as simplifying reordering.

Product usage and product package activity can be monitored and logged by the product interaction monitor. This monitoring and logging can be conducted stealthily without the user's knowledge, which can be helpful in conducting clinical trials where users may behave differently if they are aware their behaviors are being monitored. The consumable package or replaceable component with the product interaction monitor may use a wireless communication system to communicate the logged data to a remote device. In a clinical trial setting, a user can return the consumable package or replaceable component with the product interaction monitor upon completion of the trial upon which the usage information can be downloaded and analyzed for deviations from the clinical trial protocol.

These and other objects, advantages, and features of the invention will be more fully understood and appreciated by reference to the description of the current embodiment and the drawings.

Before the embodiments of the invention are explained in detail, it is to be understood that the invention is not limited to the details of operation or to the details of construction and the arrangement of the components set forth in the following description or illustrated in the drawings. The invention may be implemented in various other embodiments and of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the invention to any specific order or number of components. Nor should the use of enumeration be construed as excluding from the scope of the invention any additional steps or components that might be combined with or into the enumerated steps or components. Any reference to claim elements as "at least one of X, Y and Z" is meant to include any one of X, Y or Z individually, and any combination of X, Y and Z, for example, X, Y, Z; X, Y; X, Z; and Y, Z.

DESCRIPTION OF THE CURRENT EMBODIMENT

A product interaction monitor can be installed in or on a product package to assist in monitoring user interactions with a product package. For example, the product interaction monitor can collect data that can be utilized to provide an objective indication of whether a user followed a certain protocol, such as a directed use or a clinical trial protocol. Interactions with the product package can be used to characterize use of the product, for example to determine product inventory.

Figure 15A:
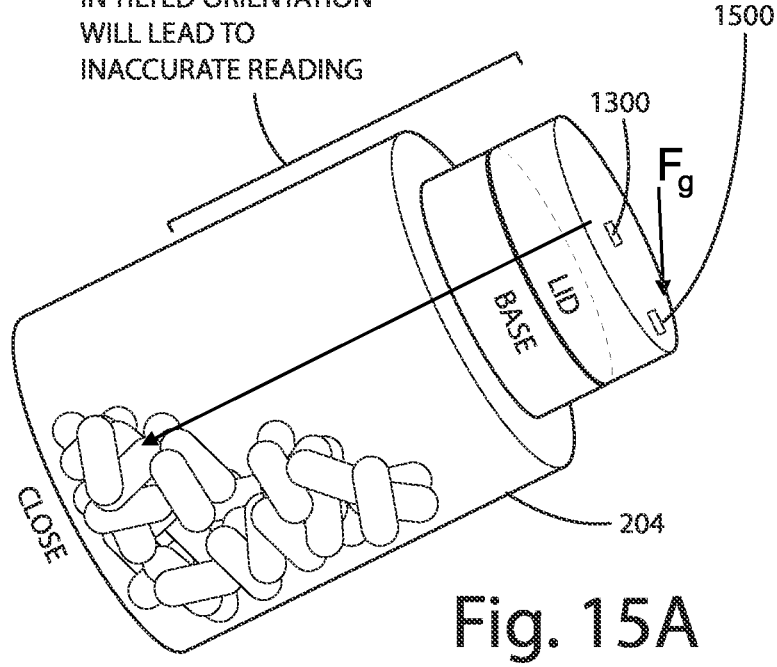
FIG. 15A illustrates a representative perspective view of a product interaction monitor with an accelerometer and time of flight sensor where the container is in a tilted orientation.
Figure 15B:
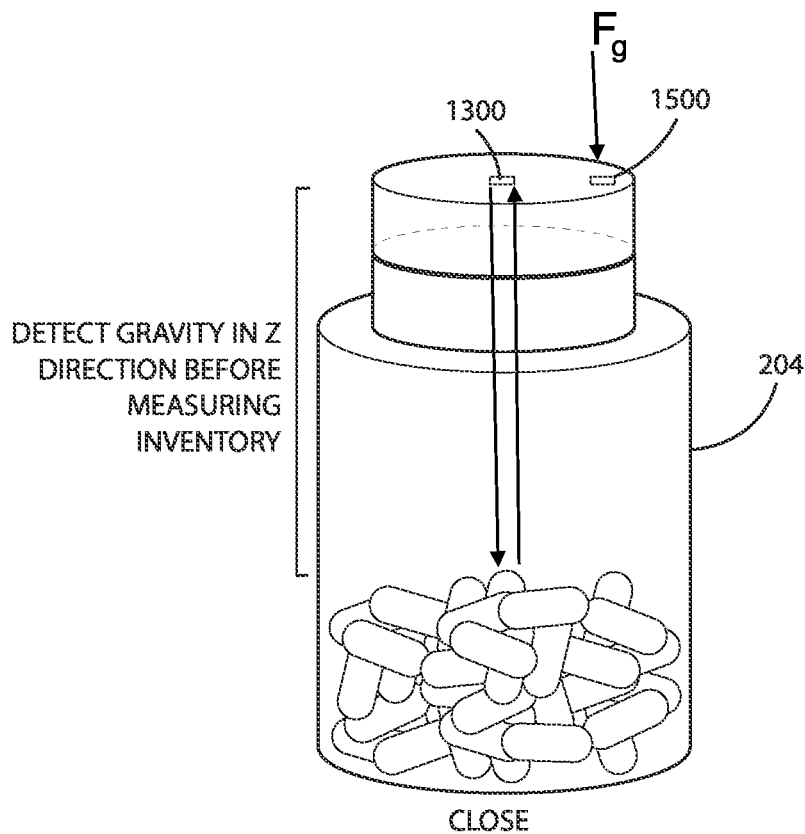
FIG. 15B illustrates a representative perspective view of a product interaction monitor with an accelerometer and time of flight sensor where the container is in an upright orientation.
Figure 16:
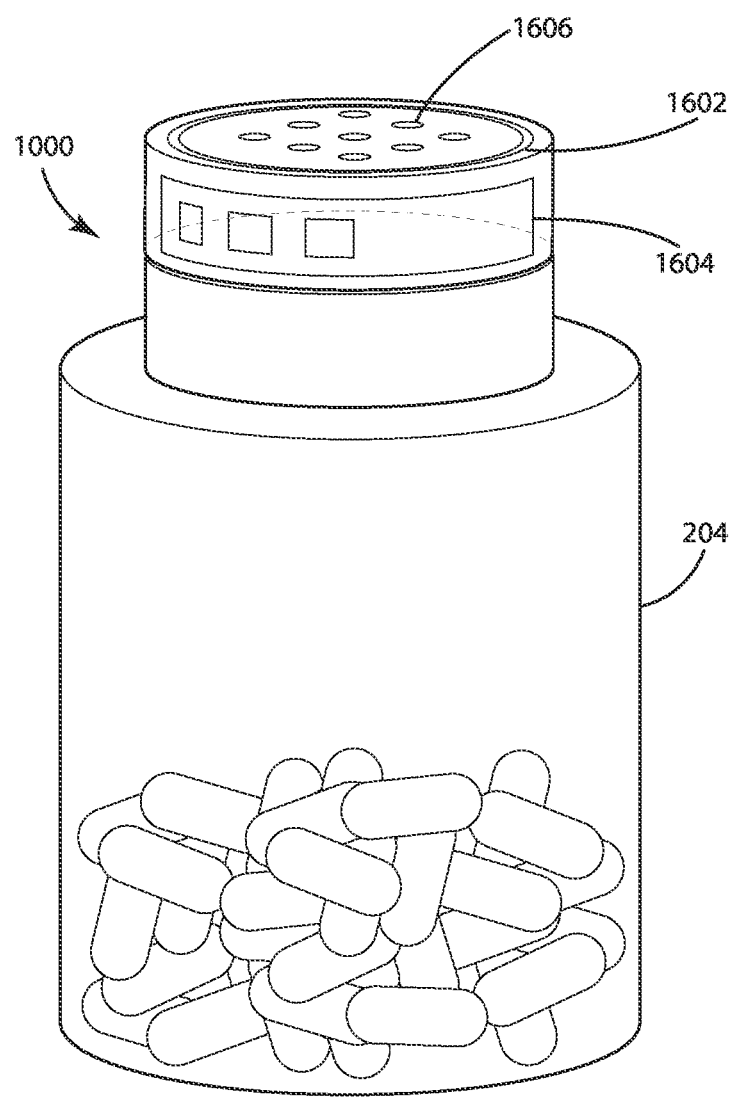
FIG. 16 illustrates one embodiment of a cap having an LED reminder, inventory display, and speaker.

The product monitor can be used to assist in monitoring one or more characteristics of product stored in the package. For example, the product monitor can assist in monitoring freshness or inventory of the product. The product monitor can assist in these determinations based on output from one or more sensors, for example product freshness may be determined based on output from a humidity sensor and/or a temperature sensor. Product freshness may also be estimated based on the number and timing of smart cap events, such as opening events, closing events, and pump dispense events. Product inventory level can be monitored using a time of flight sensor. Inventory level can also be approximated by monitoring the number of times the product is accessed/dispensed and associating each access/dispense event with consumption of a certain amount of product. For example, the characteristics of a pump event can be utilized to estimate or determine the amount of product dispensed from the container. In conjunction with a known starting amount, product inventory can be tracked over time. As shown in FIGS. 15A and 15B the accelerometer 1500 can be utilized to detect gravity in the Z direction before measuring inventory with the time of flight sensor 1300 because measuring inventory in a tilted orientation may lead to an inaccurate reading.

The product monitored by the product interaction monitor can vary depending on the application. For example, product can include powder, pills, liquids, capsules, or other types of consumable products. For example, some of the types of products that the product interaction monitor can monitor include nutritional supplements, vitamins, and medicaments. The product can come in a variety of different shapes and sizes.

Figure 2:
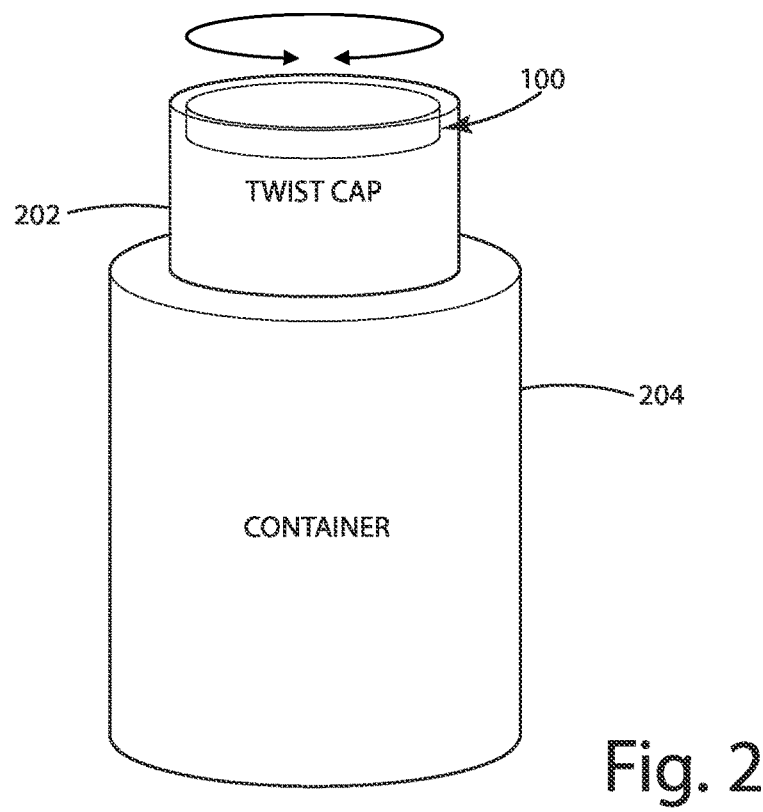
FIG. 2 depicts a representative perspective view of a product interaction monitor installed in a twist cap for a container.
Figure 3:
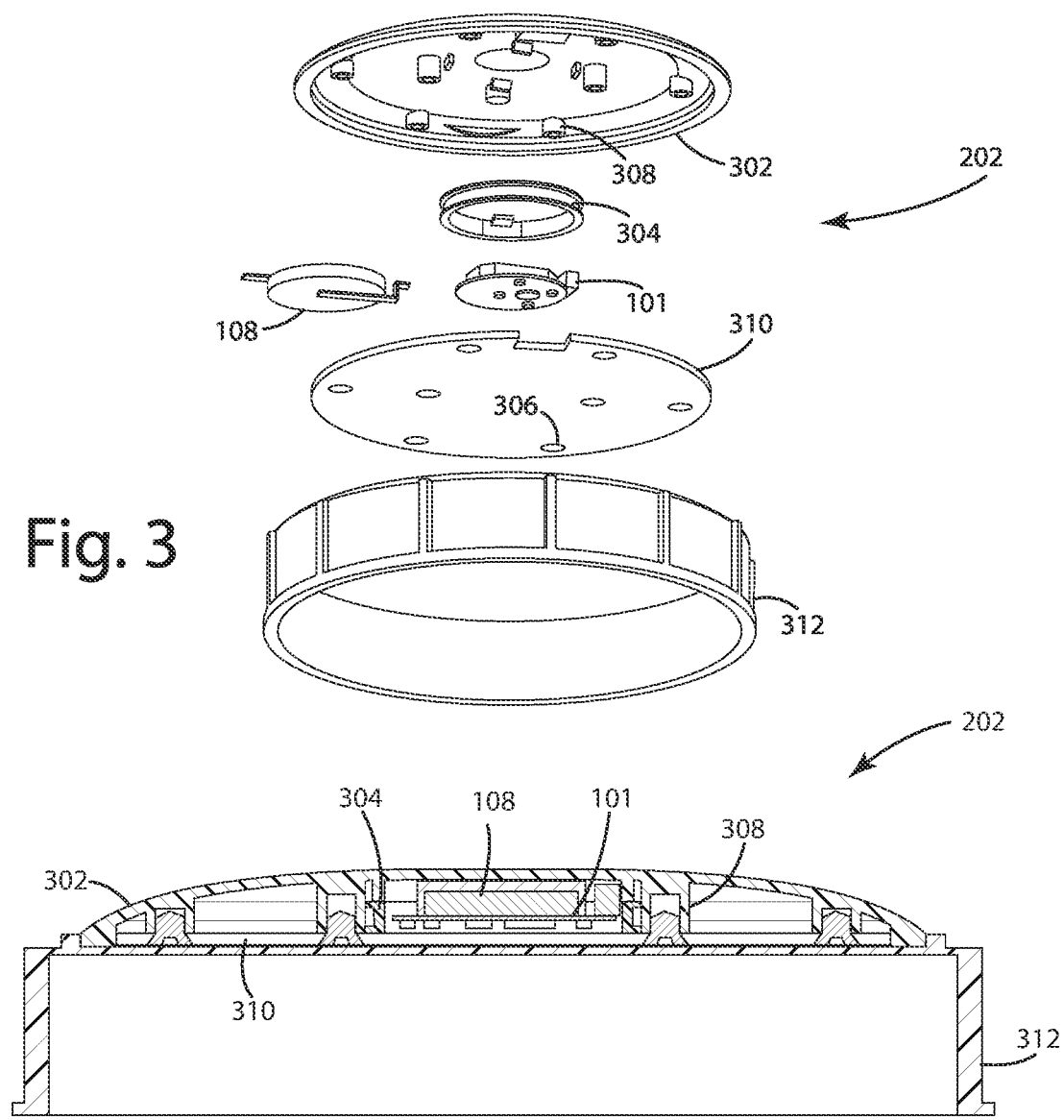
FIG. 3 is an exploded view of the exemplary twist cap.
Figure 10A:
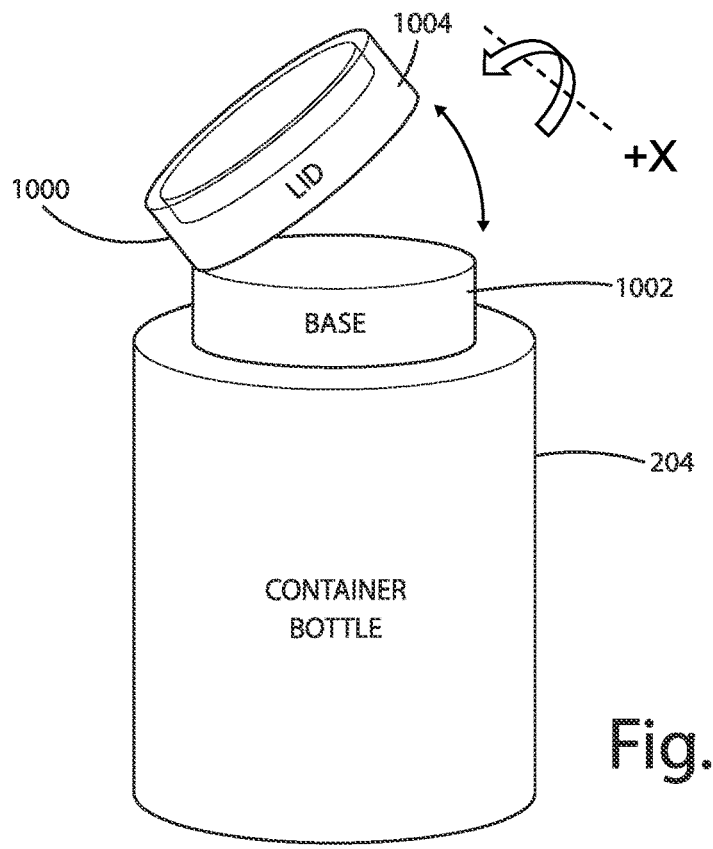
FIG. 10A illustrates a representative perspective view of a product interaction monitor installed on a flip cap for a container.

The product interaction monitor can work in conjunction with a variety of different containers. For example, a product interaction monitor can be installed in and configured for use with a variety of different flip-top caps, twist caps, and pump caps that can be installed on a product container. FIG. 2 shows an example of a twist cap that is installed and removed by rotation the cap onto a threaded container neck. FIG. 10A shows an example of a flip-top cap that is also installed and removed by rotating the cap onto a threaded container neck. In use, the flip top cap has a base and lid portion where the lid portion is opens using a hinge with the base to provide access to the container, whereas the twist cap is twisted off the container to provide access to the container.

The product interaction monitor can have a variety of different sensors that collect data about the product packaging or product within the packaging. For example, the product interaction monitor can have one or more sensors including an accelerometer, gyroscope, temperature sensor, humidity sensor, magnetometer, ambient light sensor, time of flight sensor, capacitive touch sensor and essentially any other type of sensor. In the embodiment depicted in FIGS. 1-9, the sensors include a 3-axis accelerometer and a 3-axis gyroscope. The output from the sensors can be collected and analyzed individually or in combination to provide an indication about the product packaging or the product stored in the package. For example, the product interaction monitor can be installed in the cap of a product container, such as a bottle, and one or more of the sensors can be utilized to determine when the cap of the container is opened. In one embodiment, the product interaction monitor can more accurately determine if, when, and/or for how long, the cap to a product container is opened and closed using a combination of output from a gyroscope and an accelerometer.

In some embodiments, the product interaction monitor can utilize output from one or more sensors to determine the freshness of the product in the product container. The accuracy of the freshness determination may be increased by combining output from a plurality of sensors. For example, output from a sensor capable of determining if the cap has been left off the container and output from a sensor capable of determining there has been a change in humidity and/or temperature in the product container can be combined to increase the accuracy of the freshness determination.

One embodiment of a product interaction monitor installed in a replaceable, twist-off, threaded cap for a bottle is descried in connection with FIGS. 1-9. In this embodiment, the product interaction monitor can collect data to accurately identify an open event and/or a close event by using output from a combination of two or more sensors on the product interaction monitor. In the depicted embodiment, the product interaction monitor includes a gyroscope and an accelerometer for accurately detecting opening and/or closing of the cap.

Figure 1:
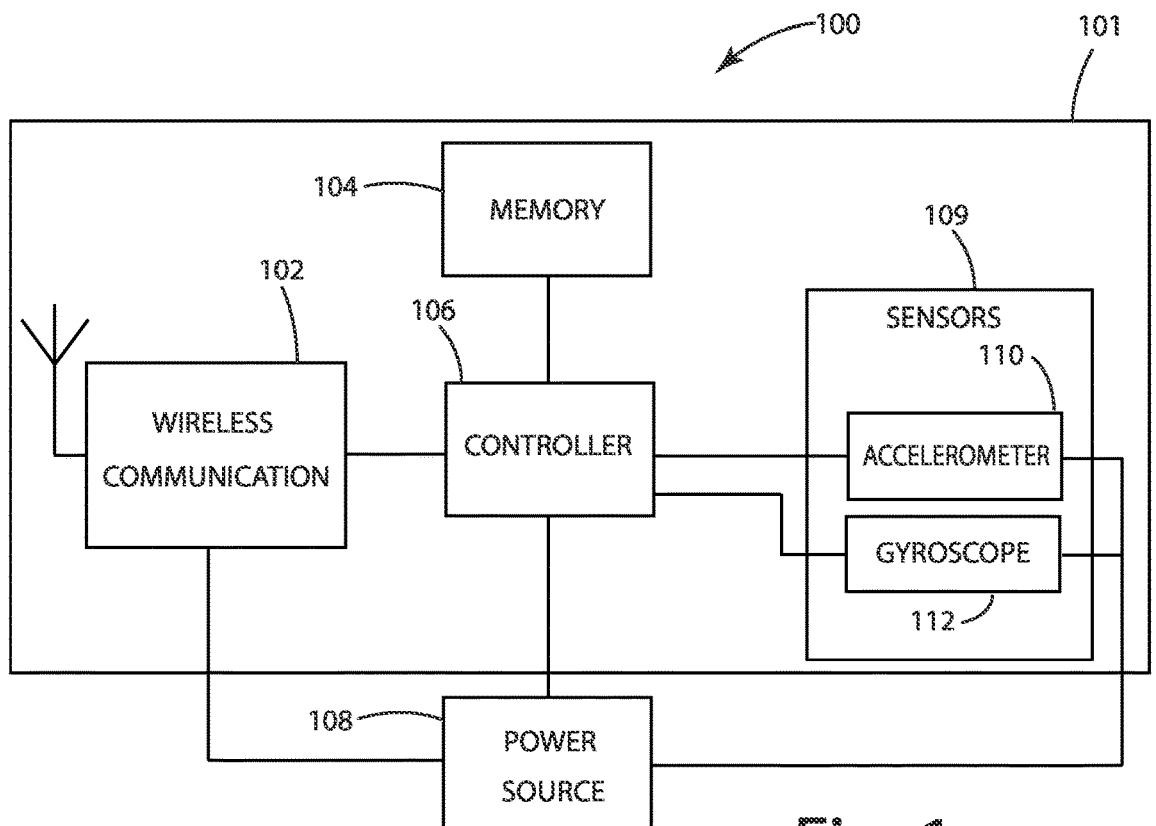
FIG. 1 is a block diagram of exemplary electronic components of a product interaction monitor that can be installed on or in a consumable package or replaceable component of a consumable package.

FIG. 1 depicts a block diagram of a product interaction monitor 100 in accordance with one embodiment of the invention. The product interaction monitor 100 includes a controller 106, memory 104, a wireless communication system 102, and sensor system 109 including an accelerometer 110 and a gyroscope 112 in this exemplary embodiment. The product interaction monitor 100 can be powered by a power source 108, such as a battery. The power source 108 can be internal to the product interaction monitor or an external power source that physically connects to the product interaction monitor. The sensor system 109 is in communication with the controller 106. The sensor system 109 can be internal to the product interaction monitor as depicted in FIG. 1 or alternatively some or all of the sensor system may be located elsewhere on the smart cap, remote from the product interaction monitor.

The controller can run software that controls the sensors, memory, and wireless communication system. The controller can instruct the sensors, including the accelerometer and gyroscope in this embodiment, to change from a low power sleep mode to an active mode. The controller can instruct the sensors when to take measurements. The controller can receive output from the sensors. The controller can be programmed to store the output in memory 104. The controller can be programmed to analyze the sensor output and store information based on the sensor output in memory. For example, the controller can store raw output from the accelerometer and gyroscope in memory. As another example, the controller can analyze the raw sensor output from the accelerometer and gyroscope to determine certain events based on predetermined criteria and the controller can store the occurrence of those events in memory. For example, referring to FIG. 7, the controller may determine and store in memory the occurrence or non-occurrence of the following events: a pick-up event 702, initial twist event 704, increment gyro trip counter event 706, lid set down event 708, lid set down duration event 710, to name a few.

Alternatively, the controller may store in memory opening events and closing events along with other information associated with those events, such as a timestamp.

The controller can communicate information using the wireless communication system. The wireless communication system can be a Bluetooth Low Energy radio or essentially any other alternative communication link. The wireless communication system can be configured to communicate with essentially any remote device. For example, the wireless communication system can be configured to communicate to a user smart phone, a display mounted to the product package or replacement product package component, or an intermediate device that can communicate to a database server on the Internet.

An exemplary smart cap assembly in accordance with one embodiment of the invention is depicted in FIGS. 2-5. These figures depict the location of the electronics and power source as well as the rest of the construction of one embodiment of a twist off cap in accordance with the present invention. This smart cap can log data from one or more of the sensors installed on the product interaction monitor in memory for later transmission over the wireless communication system 102.

Figure 4:
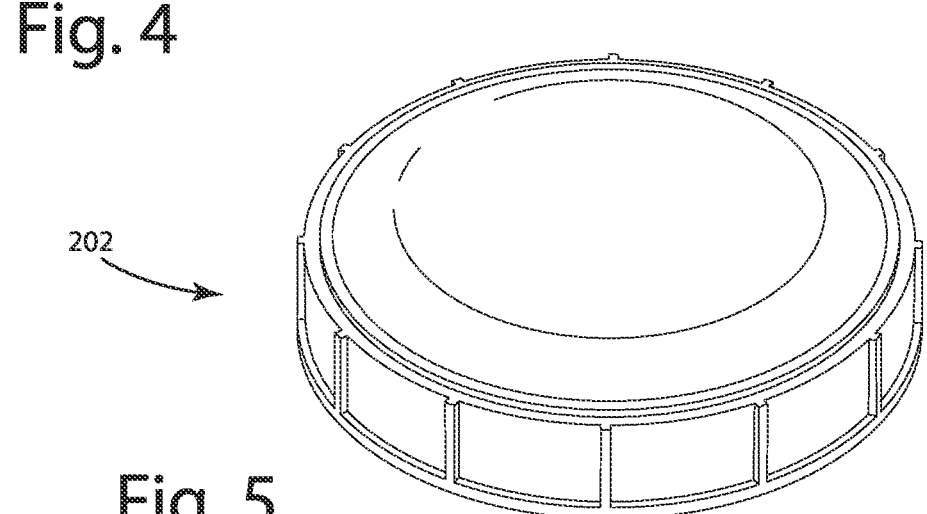
FIG. 4 is a cross section view of the exemplary twist cap.
Figure 5:
FIG. 5 is a perspective view of the exemplary twist cap.
Figure 6:
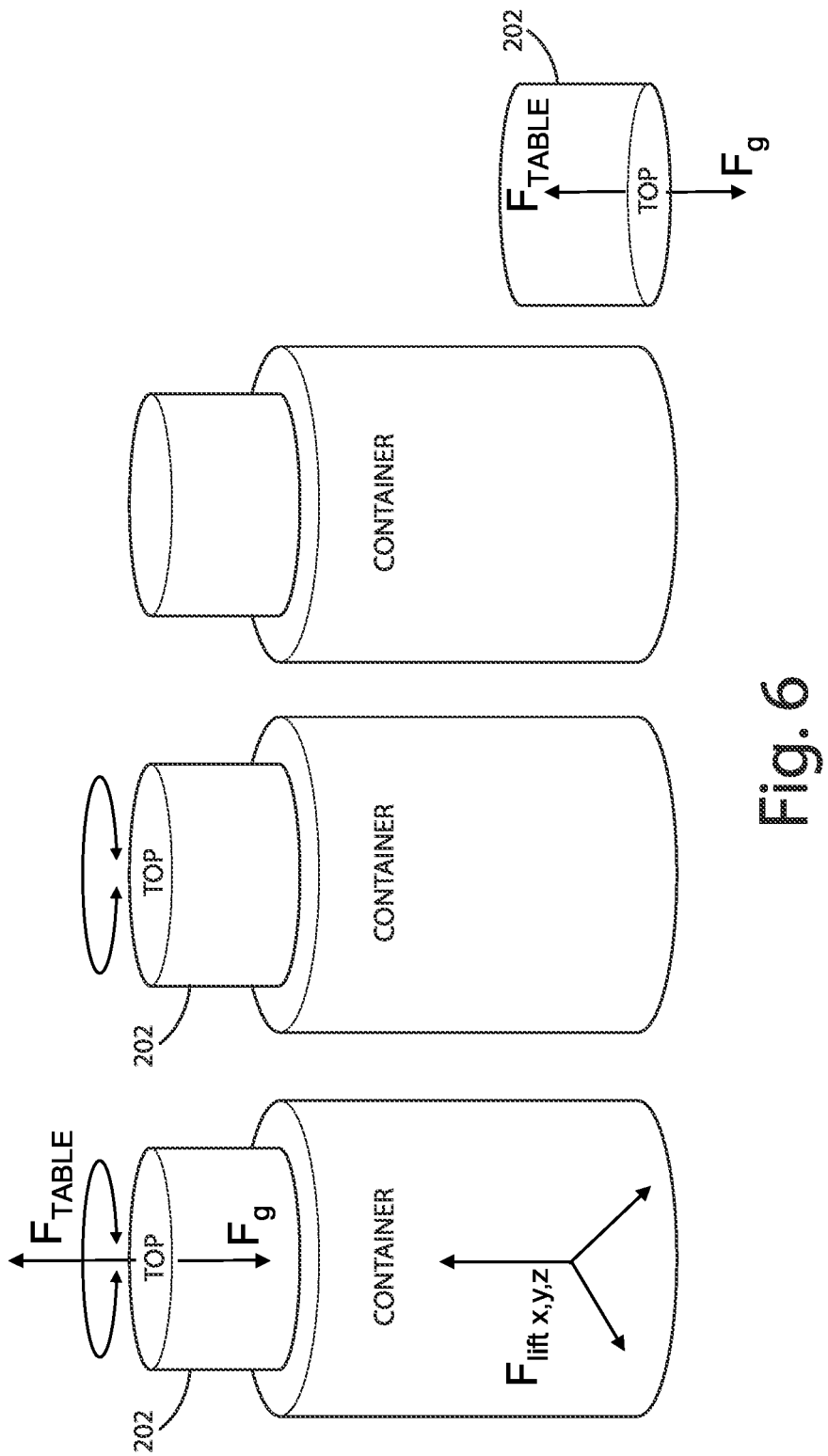
FIG. 6 illustrates forces that can be detected using one or more of a plurality of sensors on the exemplary twist cap.
Figure 7:
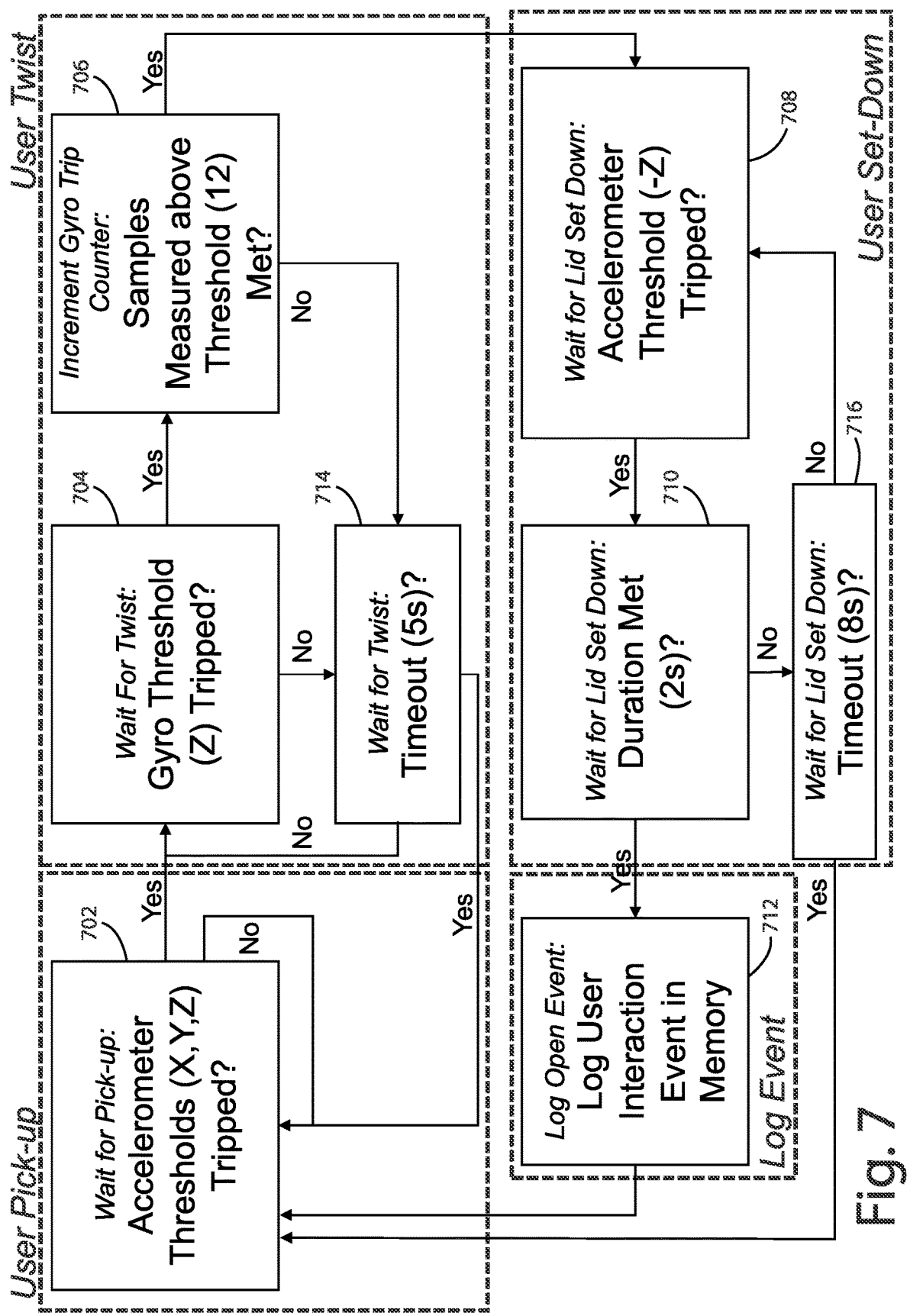
FIG. 7 illustrates an exemplary flow chart for detecting a product interaction using a combination of sensor output.

Perhaps as best seen in the exploded view of FIG. 2, the smart cap assembly of the current embodiment includes a top plate 302, an electronics retaining ring 304, a power source 108, a product interaction monitor 101, a bottom plate 310, and a threaded lip 312. Several of the components of the smart cap assembly work in conjunction as a housing to conceal the product interaction monitor from external viewing by a user. The electronics retaining ring 304 is positioned on the underside of the top plate 302. The power source 108 and the product interaction monitor 101 (or collectively 100) are positioned within the electronics retaining ring so they are retained in place during use. The top plate 302 and bottom plate 310 are joined together sandwiching the retaining ring 304, power source 108, and product interaction monitor 101, holding them in place. The bottom plate can be secured to the top plate using screws or other fasteners through the apertures 306 in the bottom plate 310 and received by the receivers 308 in the top plate 302. The top plate 302 and the threaded lip 312 are joined to provide a twist off cap for a container. A cross-section view of the smart cap assembly is depicted in FIG. 4 and a perspective assembled view of the smart cap assembly is depicted in FIG. 5.

Figure 8A:
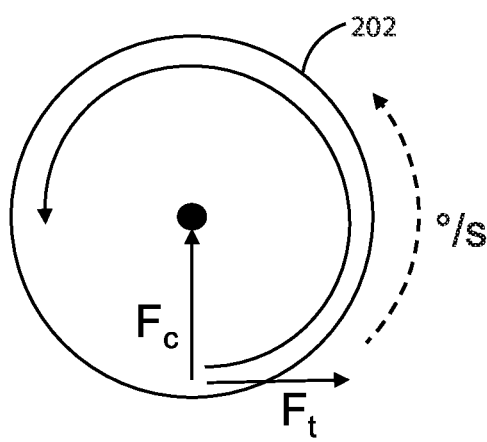
FIG. 8A illustrates rotating the twist cap in a counter-clockwise direction to unsecure and open the container along with the detectable forces by the product interaction monitor.
Figure 8B:
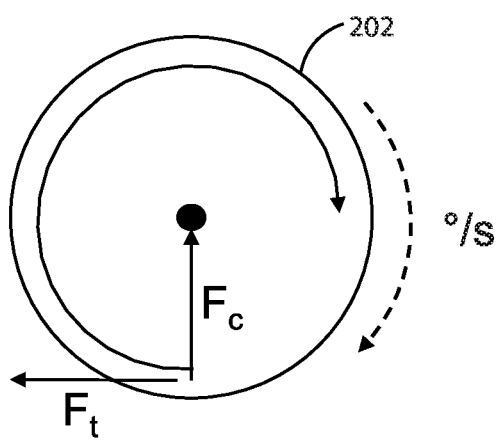
FIG. 8B illustrates rotating the twist cap in a clockwise direction to secure and close the container along with the detectable forces by the product interaction monitor.

The product interaction monitor installed in a housing of the smart cap assembly 202 which can detect open and closing of the container 204 by detecting forces on the smart cap measured by one or more of the sensors. One detection method uses an accelerometer to measure the tangential force on the smart cap. A positive change in the tangential force ($F_t$) for a duration of time can be recognized as the twisting open of a cap (FIG. 8A) and a negative change in the tangential force ($F_t$) can be recognized as the twisting close of a cap (FIG. 8B). Another detection method uses a gyroscope to measure the angular velocity around the z-axis. A negative angular velocity over a duration of time (°/s) can be recognized as twisting open of a cap (FIG. 8A) while a positive angular velocity over a duration of time (°/s) can be recognized as twisting close of a cap (FIG. 8B).

The methods above can result in false detections of cap opening and closing. Simply rotating an entire container to read a label or dropping the container and having it roll could result in false detections. The opening/closing detection accuracy can be improved and the number of false positive detections can be reduced by using a combination of sensors with various thresholds and timing sequences. That is, instead of measuring a particular threshold reading to identify an opening container event or a closing container event, a combination of thresholds, samples, and timing sequences can be used to more accurately identify the event.

Figure 17:
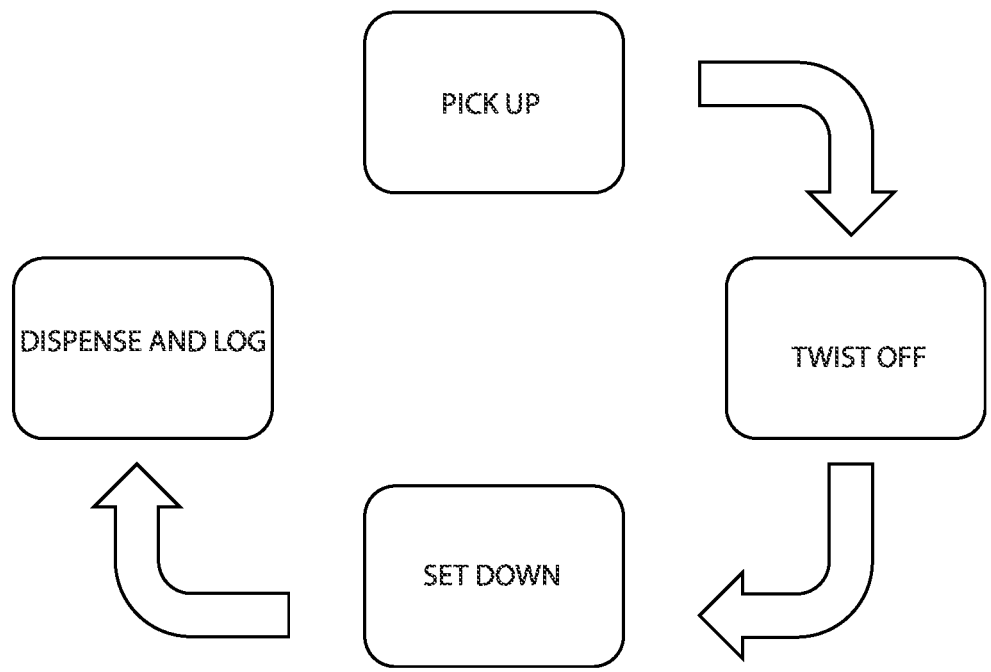
FIG. 17 illustrates a visual flow diagram for a multi-step product interaction open sequence.
Figure 18:
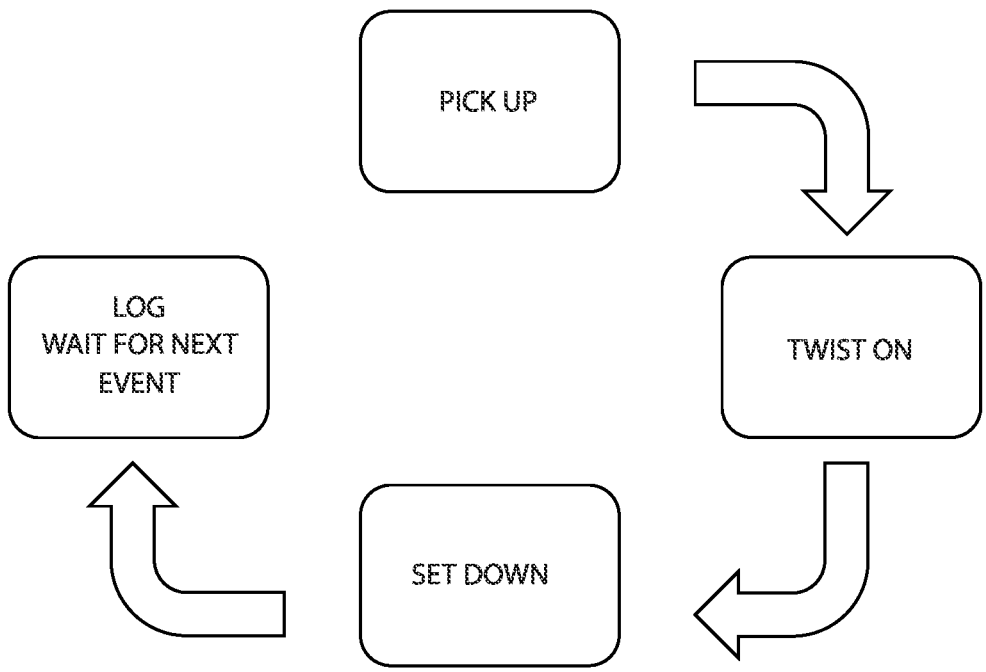
FIG. 18 illustrates a visual flow diagram for a multi-step product interaction close sequence.

FIGS. 17-18 illustrate general visual flow diagrams for a multi-step product interaction open and close sequence, respectively. One embodiment of a method for detecting an opening event for a container is described in connection with the flowchart of FIG. 7. In the method, an accelerometer sensor is initially used to monitor for a user to pick up a container 702. In this first stage of the detection, the controller determines whether there is a change in force above a predetermined threshold in any of the axes the accelerometer is monitoring. A high pass filter can be applied to help increase sensitivity so that only user applied motion is detected. This also helps eliminate the force of gravity on the sensor in any of the three axes. In the current embodiment, the threshold for this detection in any axis is 0.75 m/s$^2$. In alternative embodiments, the wake-up threshold may be different. If this threshold is exceeded, the controller moves to the second stage and enables the gyroscope. The product interaction monitor then waits for the cap to be twisted open 704, for example by measuring any or a threshold angular velocity on the gyroscope's z-axis sensor. If there is not sufficient activity on the gyroscope within a predetermined timeout period 714, then the gyroscope can be powered down or put in a sleep mode while the product interaction monitor reverts to the wait for pick-up stage 702. If the gyro threshold is tripped, the controller uses the gyroscope's z-axis sensor to accumulate angular velocity samples above a threshold of 210 degrees per second in the allotted duration of five seconds 706. In alternative embodiments, the threshold number of samples, the degrees per second threshold, and the allotted duration may each be a different value. If the controller accumulates 12 samples above this threshold, it proceeds to the third stage to wait for the user to set down the cap 708. This third stage of detection helps distinguish intentional interaction with the container, such as opening or closing the container, versus unintentional, such as picking up the container to read the label or dropping the container on the ground and having it roll across the ground.

Figure 9:
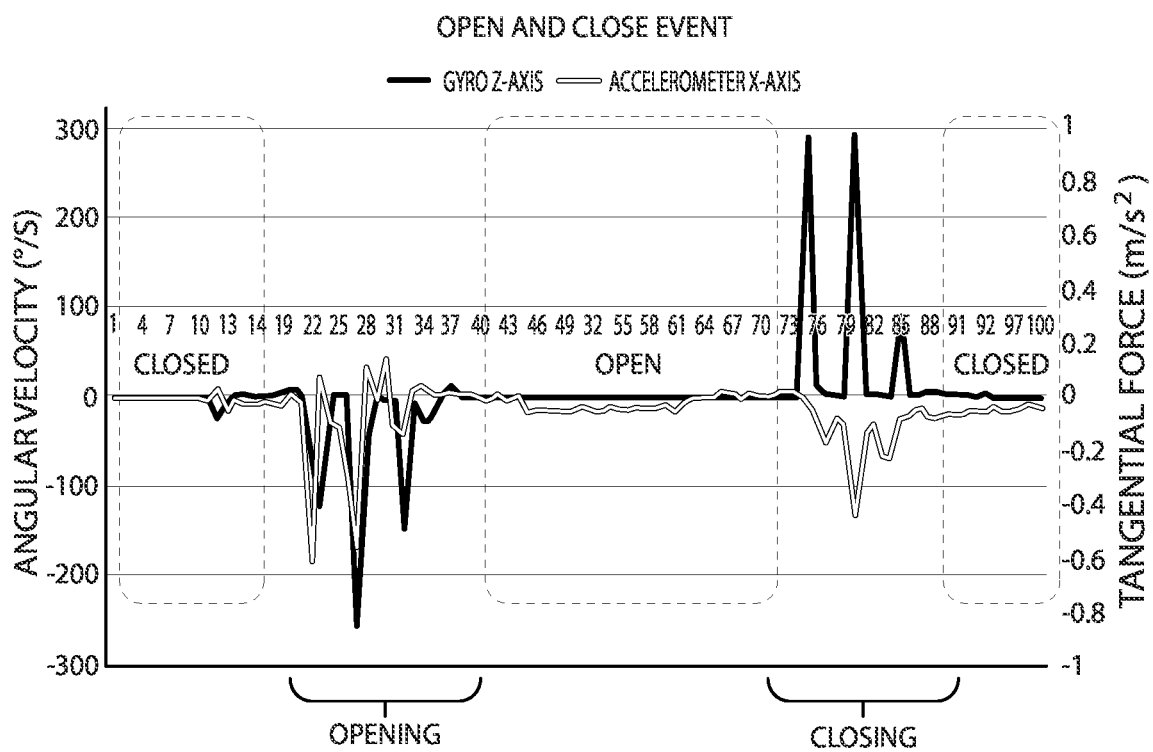
FIG. 9 illustrates exemplary output from one embodiment of the product interaction monitor sensors during a twist cap opening event and a twist cap closing event.

After a twist open is detected, the gyroscope is disabled, and the controller uses the accelerometer to determine if the user set the lid upside down while they dispense the product from the container. Typically users place the cap upside down to prevent any product captured inside the cap from falling onto their counter and also to prevent contamination of the inside of the lid and eventually the product inside the container. The controller waits for a portion of the force due to gravity to be seen in the opposing z-axis of the cap 708. If at least 3 m/s$^2$ is seen on the z-axis for 2 seconds 710 within the timeout period of 8 seconds 716 after a pickup and twist was detected, then the user open interaction is logged 712. The occurrence (timestamp) of when the cap was opened can be also be logged within the internal memory. This memory can be read out at a later time using the wireless communication system. FIG. 9 illustrates a graph of angular velocity and tangential force over time as a smart cap is opened and then closed. In response to the magnitude of the angular velocity exceeding a negative threshold for a pre-determine number of samples, the controller can identify an open event. In response to the magnitude of the angular velocity exceeding a positive angular velocity, the controller can identify a closing event.

Figure 10B:
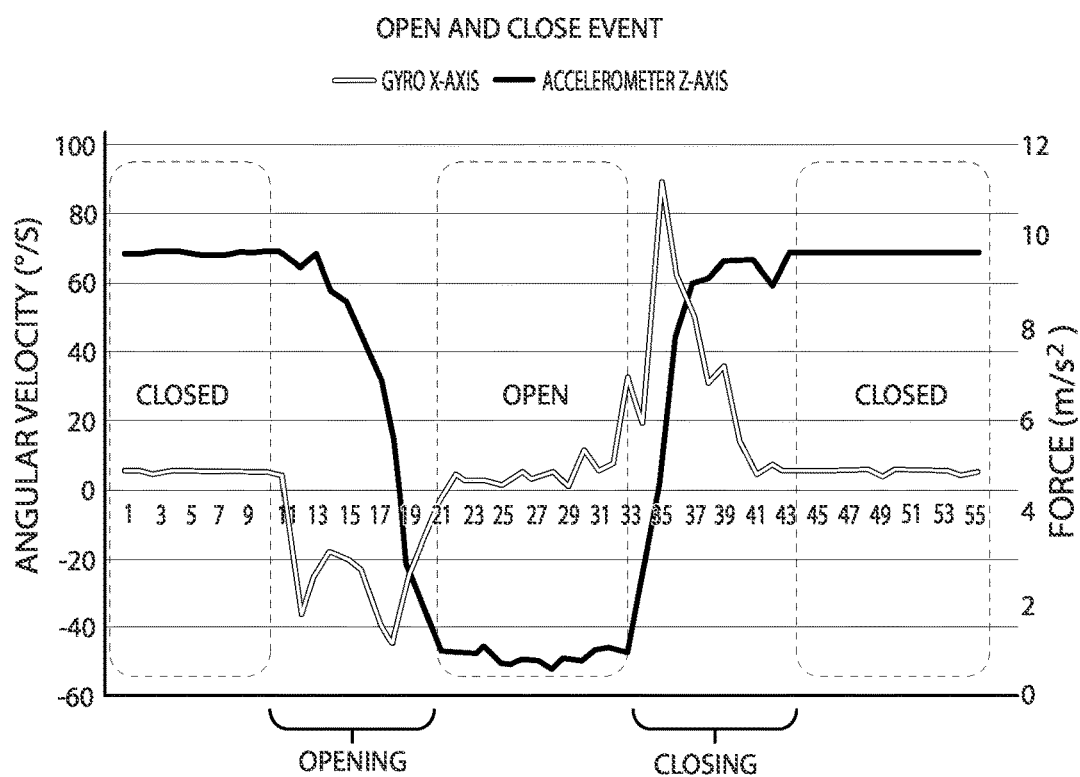
FIG. 10B illustrates forces that can be detected using one or more of a plurality of sensors on the exemplary flip cap.
Figures 11A, 11B:
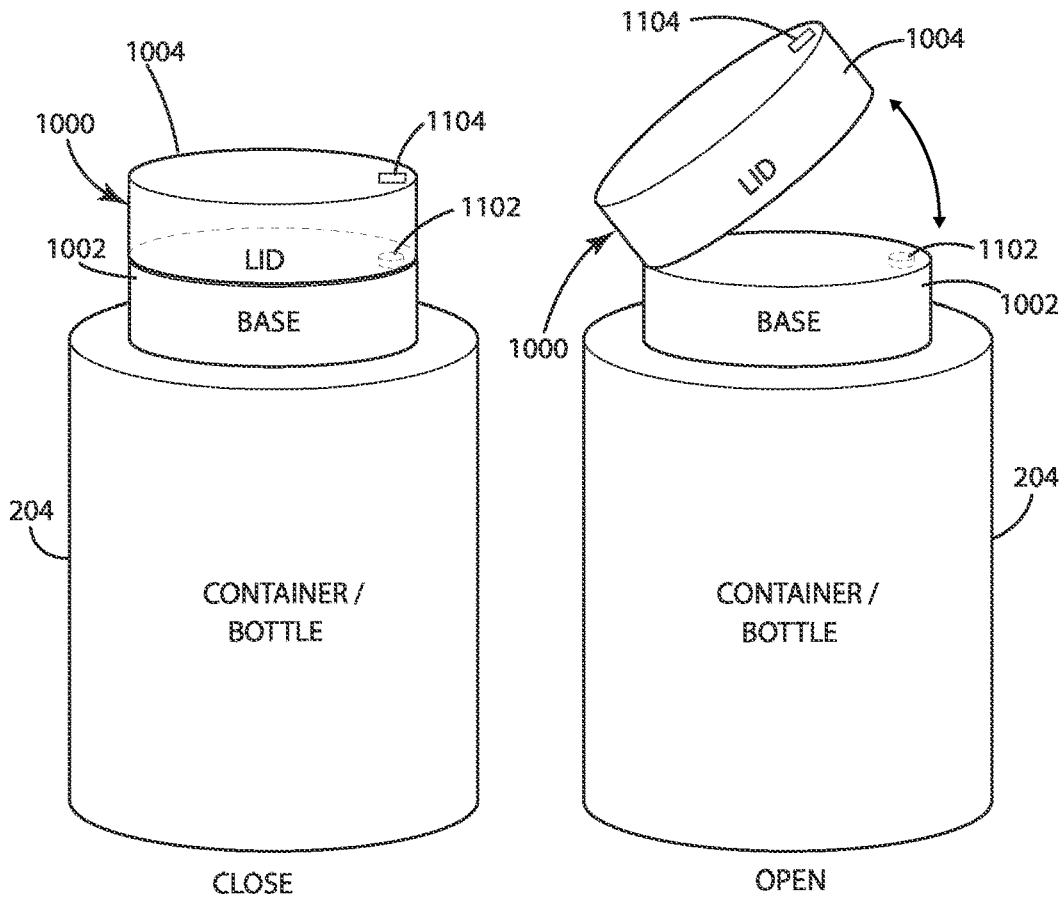
FIG. 11A illustrates a representative perspective view of a product interaction monitor with a magnetic field sensor and magnet where the flip cap is in a closed position.
FIG. 11B illustrates a representative perspective view of a product interaction monitor with a magnetic field sensor and magnet where the flip cap is in an open position.
Figure 11C:
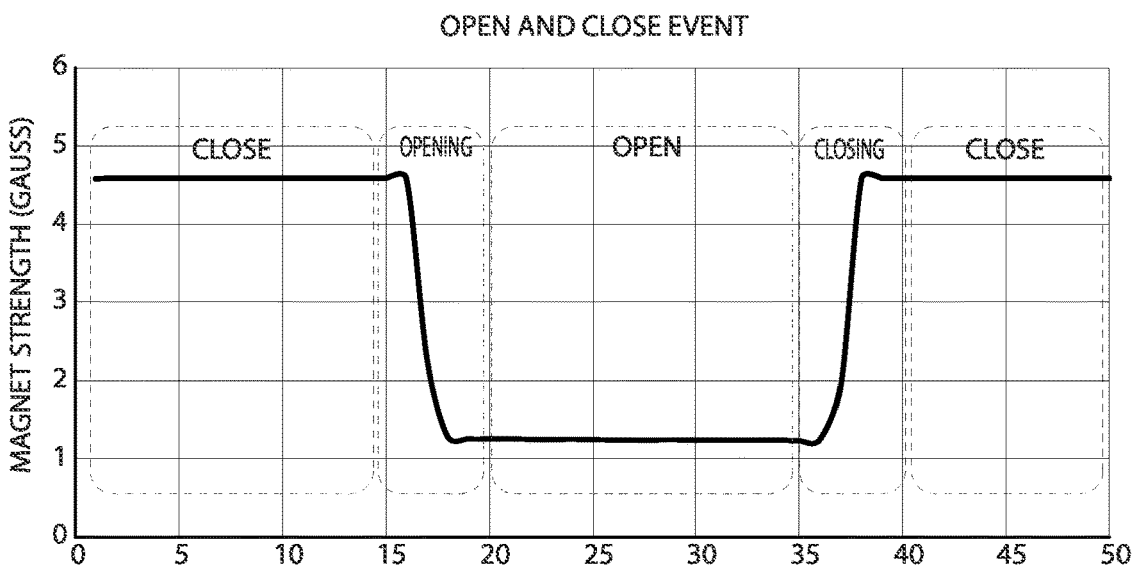
FIG. 11C illustrates forces that can be detected using one or more of a plurality of sensors on the exemplary flip cap with a magnetic field sensor.
Figure 12A:
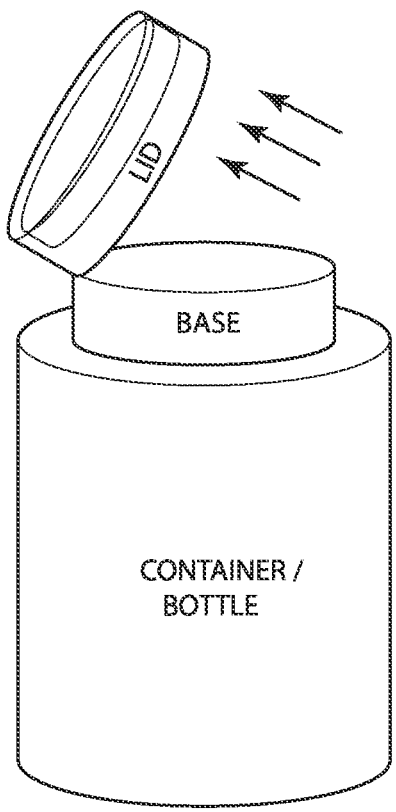
FIG. 12A illustrates a representative perspective view of a product interaction monitor with an ambient light sensor installed on a flip cap for a container.
Figure 12B:
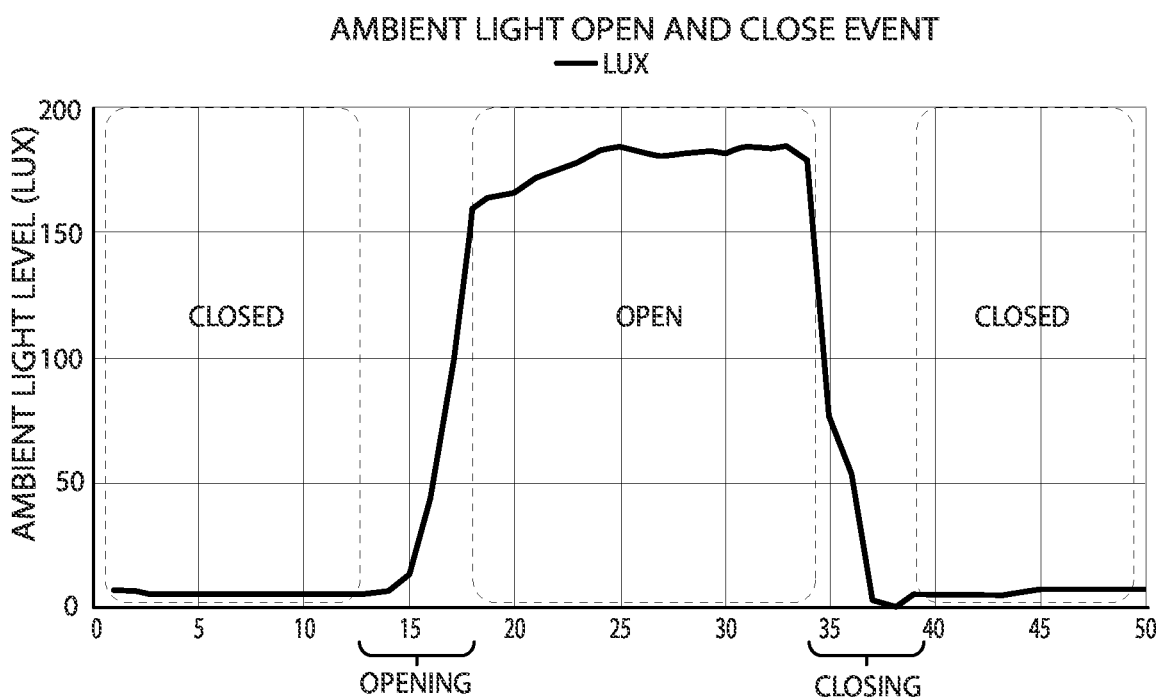
FIG. 12B illustrates forces that can be detected using one or more of a plurality of sensors on the exemplary flip cap of FIG. 10A.
Figures 13A, 13B:
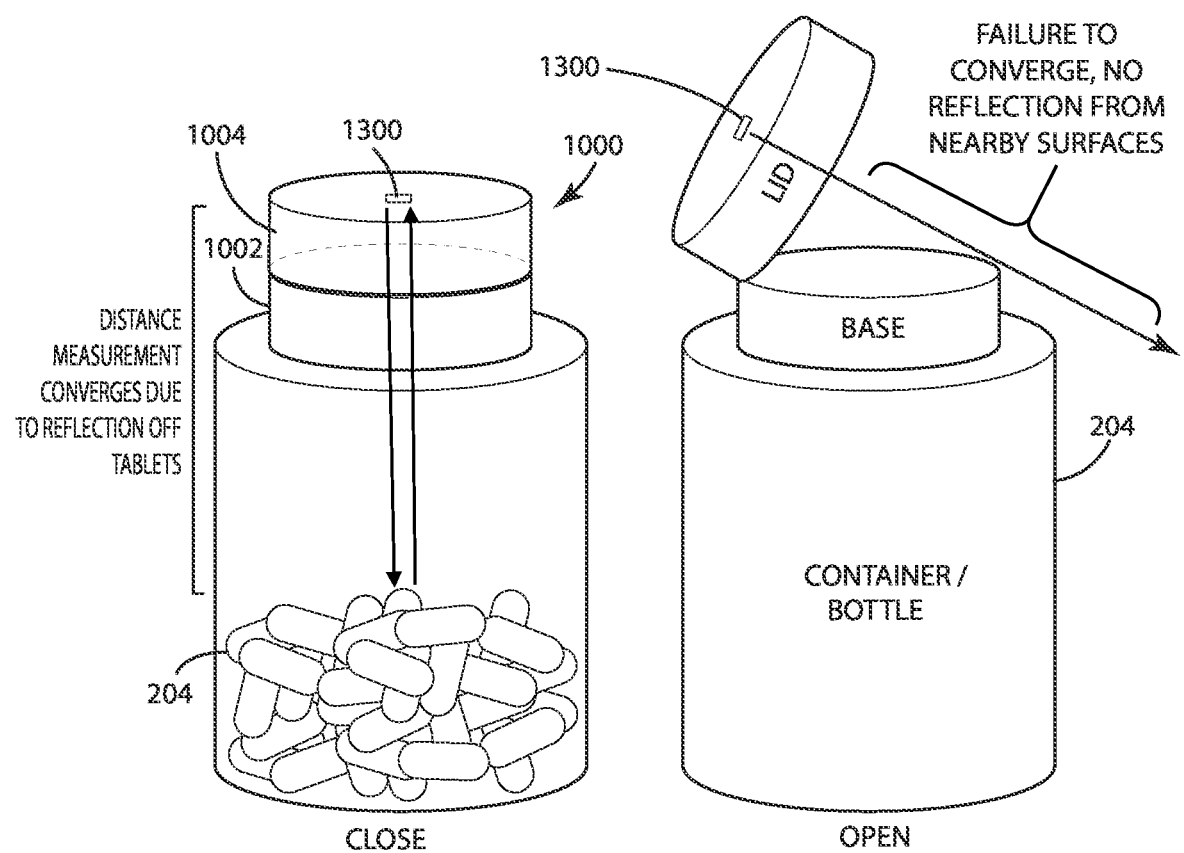
FIG. 13A illustrates a representative perspective view of a product interaction monitor with a time of flight sensor installed on a flip cap where the flip cap is in a closed position.
FIG. 13B illustrates a representative perspective view of a product interaction monitor with a time of flight sensor installed on a flip cap where the flip cap is in an open position.
Figures 14A, 14B:
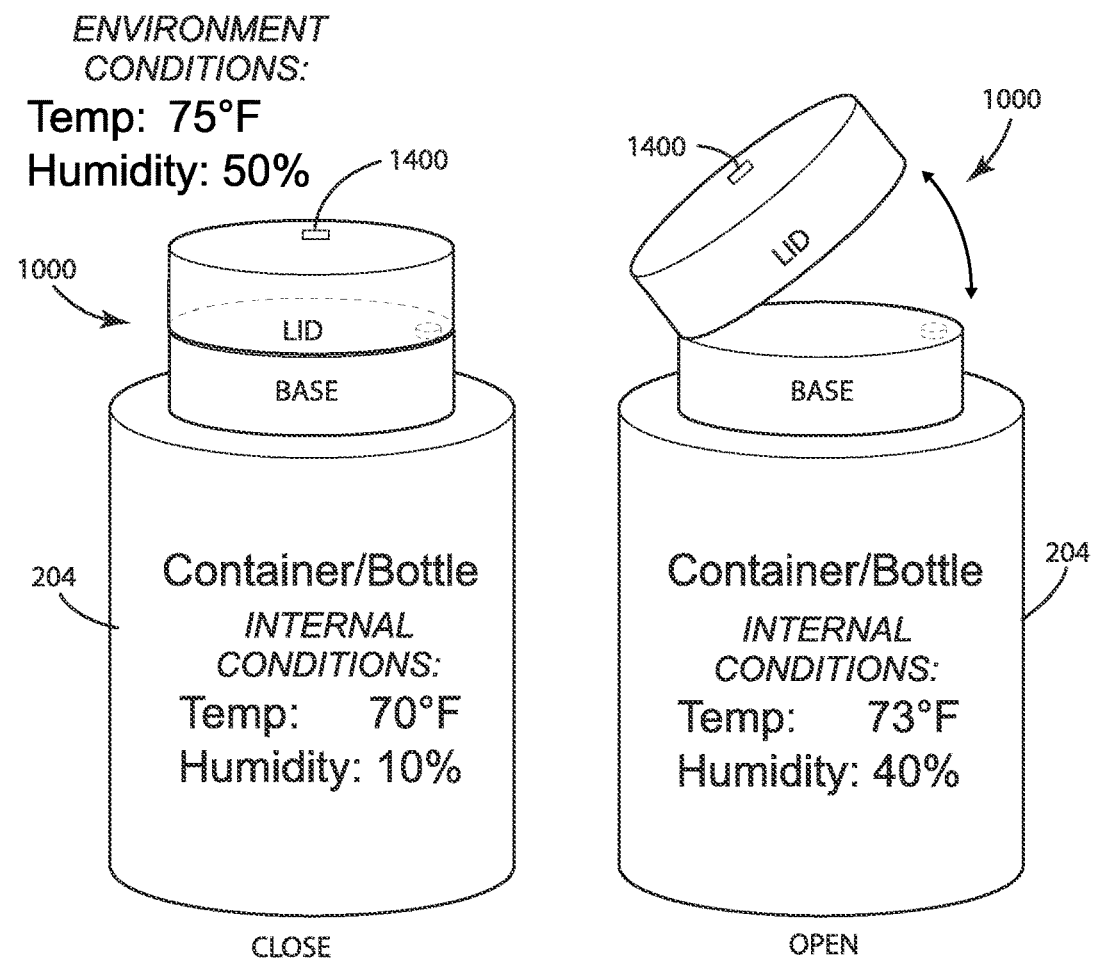
FIG. 14A illustrates a representative perspective view of a product interaction monitor with a humidity and temperature sensor installed in a flip cap where the cap is in a closed position.
FIG. 14B illustrates a representative perspective view of a product interaction monitor with a humidity and temperature sensor installed in a flip cap where the cap is in an open position.
Figure 14C:
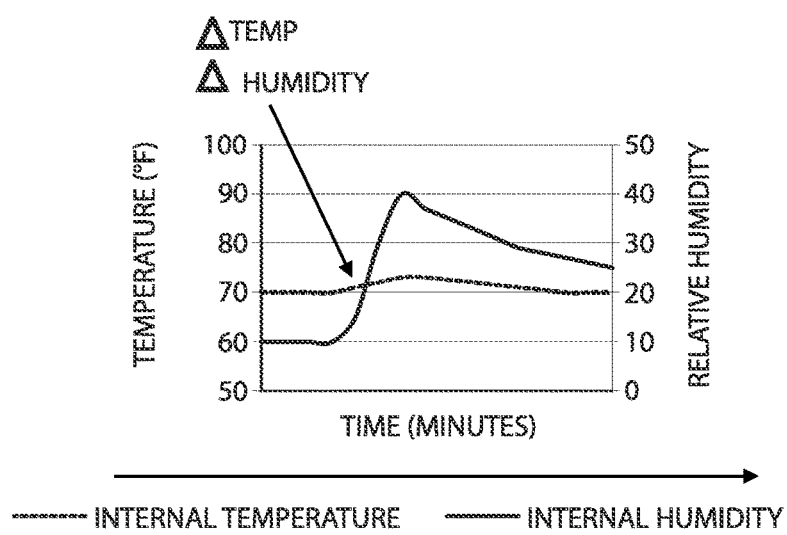
FIG. 14C illustrates measurements that can be sensed using one or more of a plurality of sensors on the exemplary flip cap of FIGS. 14A-B.

Other product integration monitors with different types of sensors can utilize similar principles to detect smart cap events. For example, FIG. 10A illustrates a flip top cap 1000 that includes a base portion 1002 and a lid portion 1004 that utilizes a combination of output from the gyro and accelerometer to identify opening and closing events (See FIG. 10B). In response to detecting a combination of negative angular velocity with the gyro and negative force with the accelerometer an open event can be determined. In response to detecting a combination of a combination of positive angular velocity and a positive force a close event can be determined. FIGS. 11A-11B illustrate a flip top cap with a magnet 1102 and magnetic field sensor 1104. FIG. 11C illustrates the magnetic strength detected by the magnetic field sensor. While the top is closed, the magnetic field strength detected is higher because the magnet is physically closer to the magnetic field sensor. While the top is open, he magnetic field strength detected by the sensor is reduced because the magnet is physical farther away from the sensor. In this way, opening and closing events can be detected by detecting a change in magnetic field strength. FIG. 12A illustrates a smart cap 1000 with an ambient light sensor installed in either the base 1002 or lid 1004. FIG. 12B illustrates data collected during an open and close event of the smart cap. The ambient light level increases as the lid is opened and decreases as the lid is closed, allowing for detecting of open and close events, respectively. FIGS. 13A-13B illustrate a time of flight sensor 1300 installed on the lid 1004 of a smart cap 1000, which can be utilized to detect a smart cap opening or closing event. FIGS. 14A-14B illustrate a temperature and/or humidity sensor 1400 installed in the interior of the smart cap 1000 and FIG. 14C illustrates exemplary data collected with these sensors. While the container is closed, the temperature sensor and humidity sensor can detect the internal conditions of the container, for example the temperature and humidity. This information can be useful for tracking the freshness of the product. The timing and thresholds for determining a smart cap event such as an open/close event or a pump event (see FIGS. 21-27) can vary from application to application. Further the precise thresholds and timings can vary depending on the calibration and configuration of the sensors.

Figure 20:
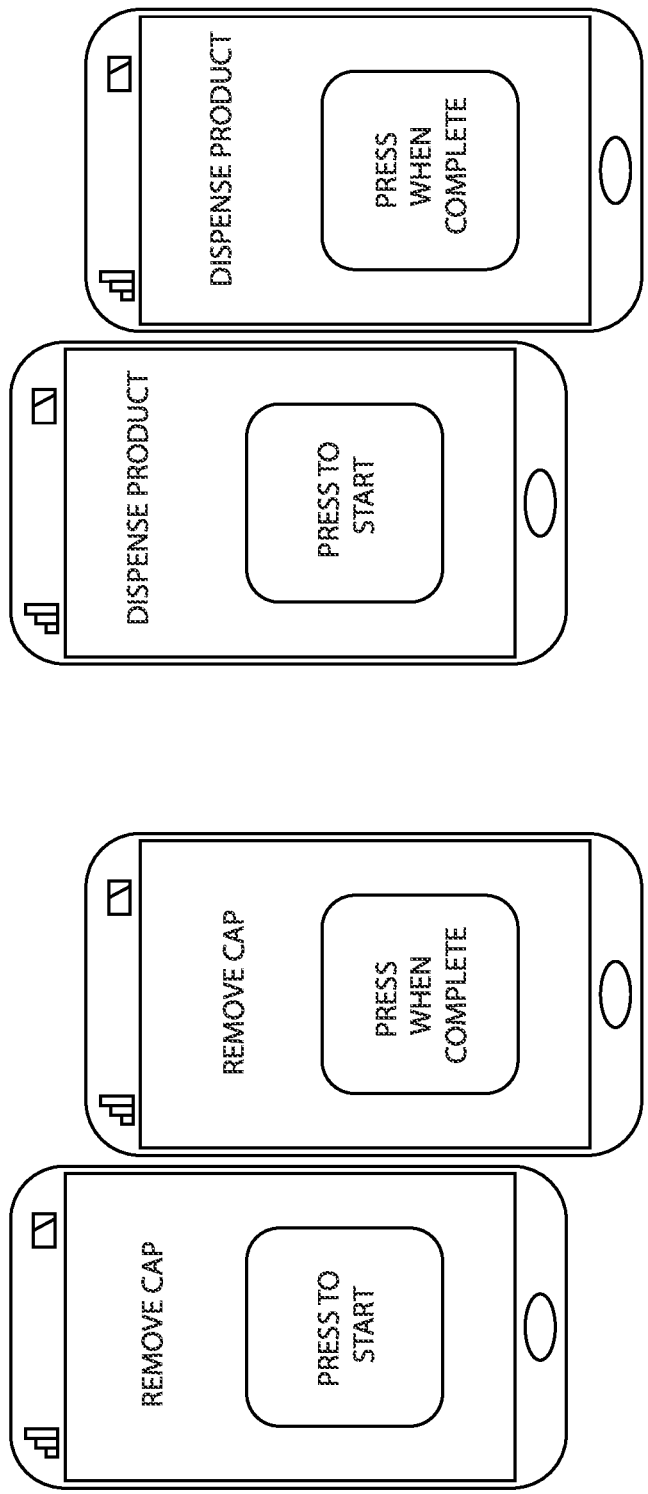
FIG. 20 illustrates a smart phone app providing instructions to and accepting input from a user.
Figure 21:
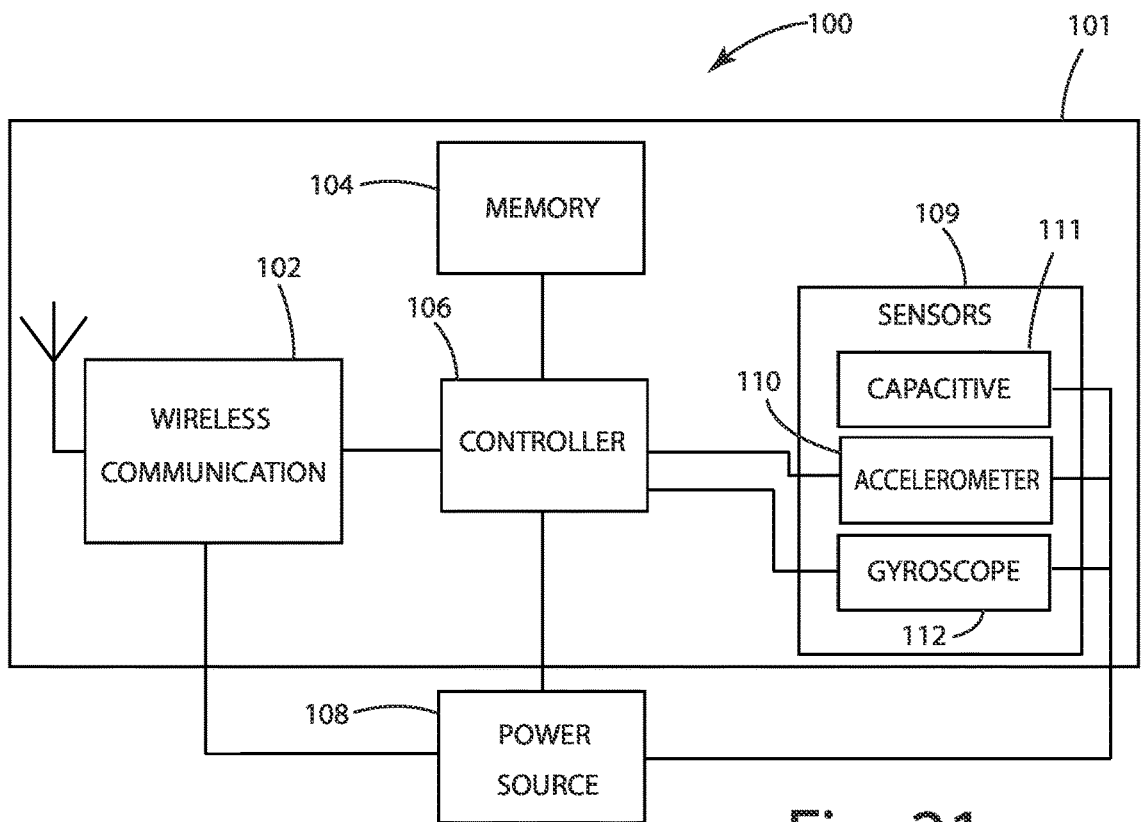
FIG. 21 illustrates a block diagram of the Product Interaction Monitor, including a capacitive sensor.
Figure 22:
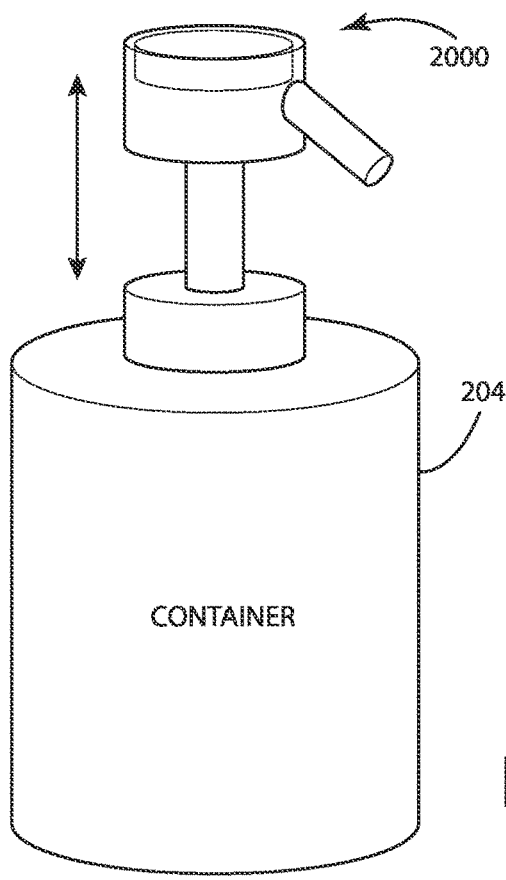
FIG. 22 illustrates a diagram of a fluid pump dispenser and container.

In a clinical setting, a user may be provided with specific instructions to interact with the product in a specific manner, such as the method described above in connection with FIG. 7. However, not all consumers may interact with the package in the instructed fashion. The product interaction monitor may increase accuracy by use of a "training" phase. In this phase, the user is guided by instructions, e.g., an application on a mobile device, to open the package. In the first stage of training, the user is instructed to remove the cap, and indicate when that task is completed, e.g., by interacting with the application on a mobile device. During this phase, the twist speed and duration are recorded for that particular user, for example by being associated with a user profile. In the second stage of training, the user is instructed to dispense the product from the container as they normally would. During the second phase, the set down angle and duration are recorded for that particular user and associated with the profile. In each stage of training the sensors record the event and calibrate the associated thresholds of the different phases of removal. An application uses a wireless link between the device and the cap to indicate when this phase of training is complete. After completing this task, the thresholds can then be adjusted to meet interaction characteristics of that particular user, the thresholds and characteristics can be stored with the user profile. The training phase can be conducted with assistance from a smart phone, as illustrated in FIG. 20.

Figure 19:
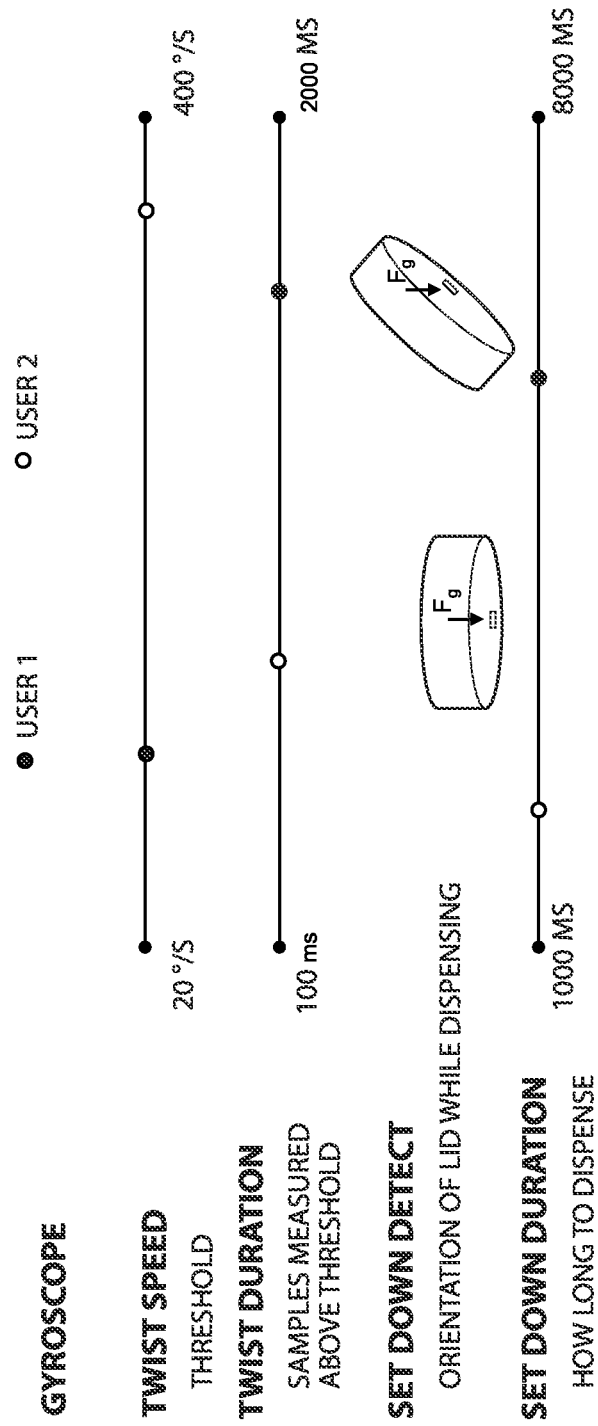
FIG. 19 illustrates exemplary trained thresholds for specific users for the product interaction monitor.

This training information may be used to identify a specific user based on their smart cap characteristics. The characteristics for tracking and adjusting may include a variety of different characteristics associated with dispensing, opening/closing, or otherwise utilizing the smart cap. For example, characteristics that can be associated with a user in a user profile utilizing a twist off smart cap are illustrated in FIG. 19 and can include peak twist speed (threshold), twist duration (samples measured above threshold), orientation of the lid while product is dispensed, dispense duration based on the duration the cap was off of the product package. In alternative embodiments, additional, fewer, or different characteristics can be tracked in the user profile and utilized to identify a specific user. These characteristics can be collected during a training phase guided by instructions, for example instructions provided during a clinical trial, or alternatively may be collected throughout normal use of the smart cap. The characteristics can be processed, for example by taking an average of multiple trials. Additional, fewer, or different characteristics can be collected for different types of smart caps. For example, a pump dispenser may track the average pump speed and average number of pumps for each pump event. The thresholds and timings can then be calibrated within acceptable boundaries for a particular user based on the training set for tracking inventory or consumption, which can increase smart cap event detection accuracy.

One embodiment of a method for detecting a closing event for a container is described in connection with the flowchart of FIG. 18. Similar to monitoring and recording the removal of the cap, the replacement of the cap can also be tracked. The same thresholds that were used for detecting an open twist event can be used to detect a close twist event in the opposite direction after the cap is returned to the container. Referring to FIG. 18 starting with picking up the lid, the pickup motion is similar to the first stage of detection when detecting the removal. The twist on motion s the same, but opposite to that of the twist off motion. The set down of the entire container and lid is the same as setting the lid down when it was removed (see FIG. 6). The occurrence (timestamp) of when the cap was replaced can be also be logged within the internal memory. This gives useful information like how long the contents may have been exposed to the outside environment (indicator of freshness) and how long it takes a user to interact with the contents (indicator of ease of use).

Compliance of product usage by a user can be monitored stealthily without the user's knowledge. The smart cap for a container can be provided with the product interaction monitor hidden from view of the user. For example, the product interaction monitor and any other circuitry can be hidden from the view of a user viewing the smart cap from an external perspective. For example, the product interaction monitor can be installed in the top portion or collar of the smart cap, sandwiched between two plates such that the smart cap is substantially visually indistinguishable from a conventional container cap from an external viewing perspective.

Data from the product interaction monitor can be collected stealthily. For example, the smart cap may not have any visual or other indication each time the user removes or returns the smart cap to the container. This information can be collected by the product interaction monitor as compliance data by either recording information about the opening and closing events in memory and/or transmitting such data to a third-party device, without indication to the user.

Stealthily collecting product interaction monitor compliance data can be especially useful during a clinical trial.

For example, the user compliance or reliability data can be useful in determining product efficacy or safety based on a 'per protocol analysis' (PP) vs. an 'intent to treat' analysis (ITT). PP analysis refers to the analysis of only those subjects in the study who did not deviate significantly from the instructions in the clinical study protocol. ITT analysis refers to the analysis of every single study subject, including subjects with significant deviations from the instructions in the protocol. Data from the product interaction monitor can be used to identify those subjects who followed the instructions in the protocol and therefore which subjects should be included in the PP analysis. Further, these data can be used to exclude from future clinical trials those subjects who deviate significantly from the protocol instructions.

The product interaction monitor can also be useful to collect compliance data stealthily in other situations such as by a concerned caretaker that is monitoring a user's compliance or a re-supplier monitoring to inform resupply decisions.

An alternative embodiment of a product interaction monitor installed in a replaceable, pump dispenser cap is described in connection with FIGS. 21-27. The product interaction monitor utilizes similar components as the product interaction monitor described in connection with FIG. 1. In this embodiment, the product interaction monitor can collect data to accurately identify a pump event instead of open/close events. A pump event can include one or more pumps of the pump dispenser. A pump event can be detected using output from one or more sensors included in the product interaction monitor. In the depicted embodiment, the product interaction monitor 100 includes an accelerometer 110 and a capacitive touch sensor 111 and utilizes a combination of output from them to accurately detecting pumps of the pump dispenser cap. Although a gyroscope is depicted in the FIG. 21 block diagram the current embodiment does not utilize the gyroscope 112 and in some embodiments it may be left out of the construction entirely. Alternative embodiments may utilize a gyroscope or another sensor in combination with the accelerometer 110 and capacitive touch sensor 111, for example to further increase the accuracy of the product interaction monitor.

Figure 23:
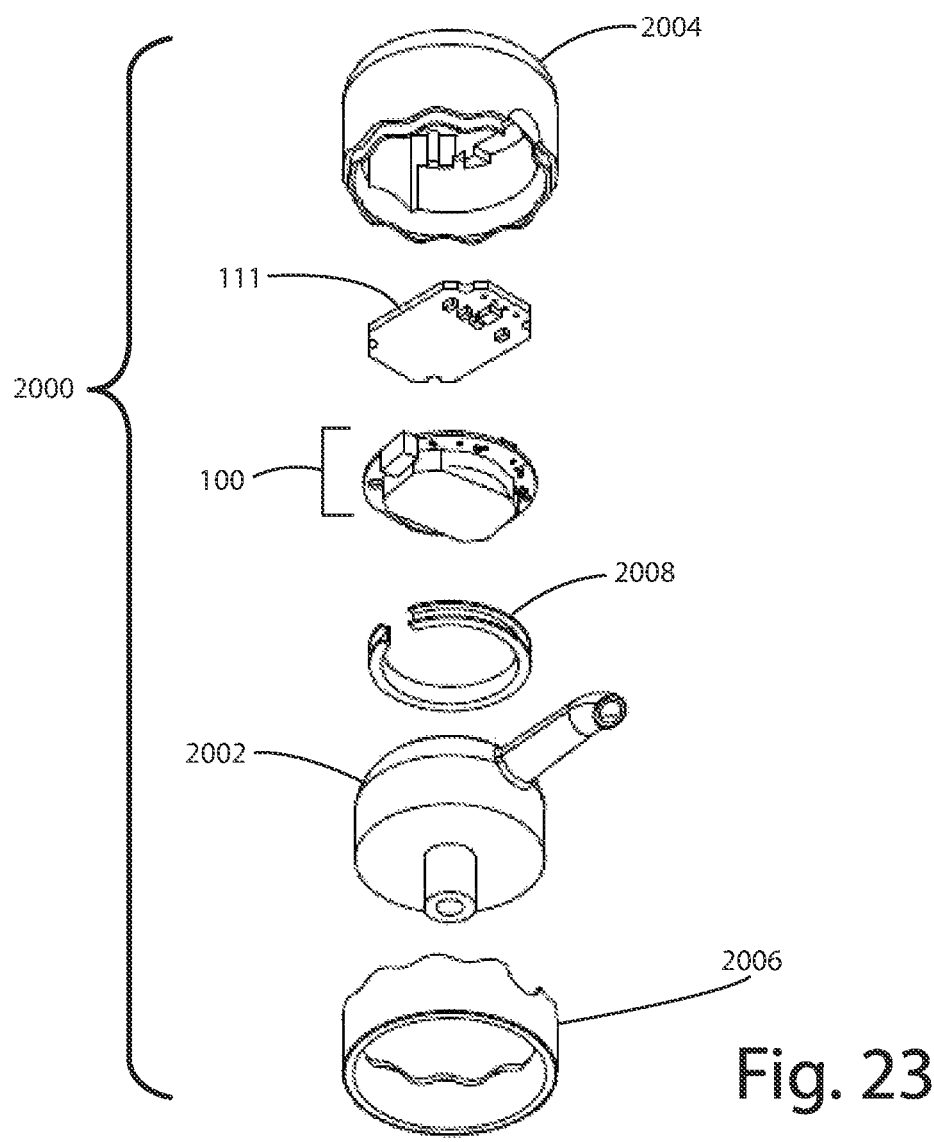
FIG. 23 illustrates an exploded view of the pump dispensing top containing a product interaction monitor.
Figure 24:
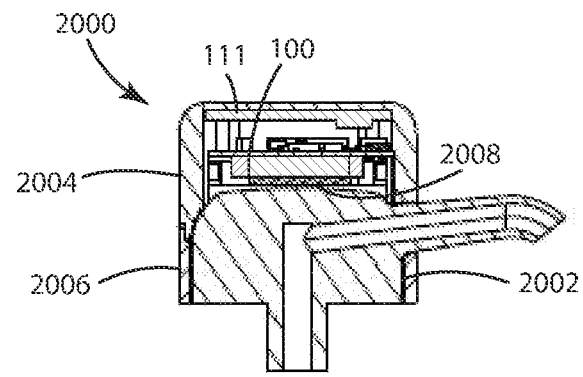
FIG. 24 illustrates a cross sectional view of the pump dispensing top containing a product interaction monitor.

In one embodiment, a fluid dispensing pump 2000 is provided. The fluid dispensing pump may include a product interaction monitor 100, power source 108, and sensor system 109 for detecting a user touching the smart cap and/or the efforts used to dispense fluid by pumping action. FIGS. 21-24 show several exemplary views of the fluid dispensing pump embodiment that provide additional information about the position of the product interaction monitor, power source and sensor(s) as well as the rest of the construction of the pump dispenser. FIG. 23 illustrates an exploded view of the fluid dispensing pump 2000 hat shows the top collar 2004, bottom collar 2006, fluid path director 2002, retaining ring 2008, product interaction monitor including battery 100, and capacitive sensor 111. In the depicted embodiment, the accelerometer is installed on the product interaction monitor, while the capacitive sensor is a separate sensor in communication with the product interaction monitor.

It should be understood that sensors of the product interaction monitor can be included physically within the housing of the product interaction monitor or they may be individual sensors in communication with the product interaction monitor Like the product interaction monitor described above in connection with the twist-off cap embodiment, the product interaction monitor installed in the pump dispenser cap also can perform data logging of any user related interactions with the dispenser. The product information may be made available remotely, for example by transmitting the data over a wireless link.

In one fluid dispensing pump embodiment, the user interaction detection is achieved through a combination of two sensors. The first sensor, a capacitive sensor, is located within proximity of the top collar of the pump underneath a thin layer of plastic. This capacitive sensor changes its capacitance when something external (e.g., a user) comes into proximity of the sensor. The capacitive sensor is used to determine that a user is interacting with the pump, removing false pump detections (e.g., if a user simply picks up the container). The second sensor, a single axis accelerometer, is configured to measure force in the z-axis. The up and down motion of the pump will create both positive and negative accelerations measurable by the accelerometer.

Users may dispense fluid with various efforts. For instance, a user may touch the top of the pump and exert a downward force to cause fluid to flow. When the pump has been fully depressed, the user may remove their touch from the pump and the pump returns to the home position. Another user may touch the top of the pump and while maintaining a constant touch, repeatedly alternate between exerting a downward force and allowing the pump to return to its home position to dispense larger amounts of fluid using multiple pumps. Alternate scenarios may exist, including the pump not being allowed to fully return to the home position before a downward force is again exerted during multiple pumps. The controller can be configured to quantify these various efforts to determine user interactions within the product interaction monitor.

Figure 25:
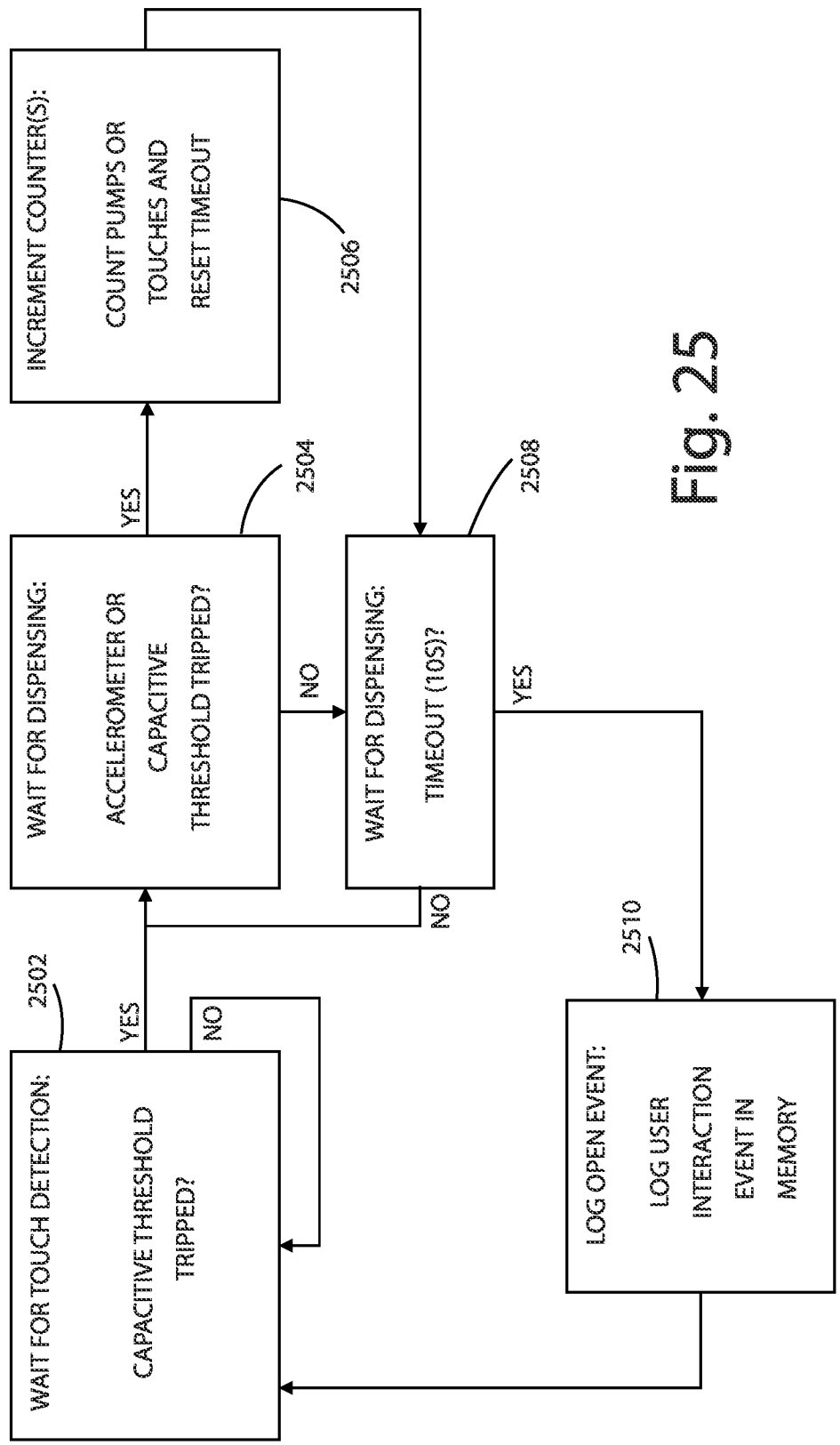
FIG. 25 illustrates a flow diagram of controller logic.

FIG. 25 illustrates an exemplary flow diagram that can be implemented in a controller in the fluid dispensing pump embodiment in order to track smart cap events, such as pumps of the pump dispenser and/or touches of the smart cap. For lowering power consumption, the controller may initially configure the accelerometer in the off or low power state while it is waiting for the touch detection to occur. The controller can be programmed to wait for dispensing 2502 by periodically (for example, about every 500 ms) checking the capacitive sensor output to determine if a user has touched the top of the pump. If the capacitive sensor has exceeded a predetermined threshold, the controller then configures the accelerometer to an on state where it measuring acceleration and waits for dispensing 2504. In the current embodiment, the accelerometer is programmed with a 119 Hz sample rate with high pass filter enabled. These settings provide adequate acceleration data while reducing noise and other unwanted forces from interfering with the intended signal.

Once the capacitive touch threshold has tripped and the system is in a waiting for pump dispensing state 2504, the controller starts an internal timer to monitor the duration of the pump dispensing event. The controller actively monitors and increments separate counters 2506 for both the number of capacitive touches on the top of the pump as well as the number of accelerometer readings that indicate a pump has occurred. The controller will reset a second timer that will timeout 10 seconds after the last touch or pump was detected 2508. After this timeout occurs, the controller can log a time stamp, duration of pumping interaction, number of touches, and number of pumps to the memory located within the product interaction monitor 2510.

Figure 26:
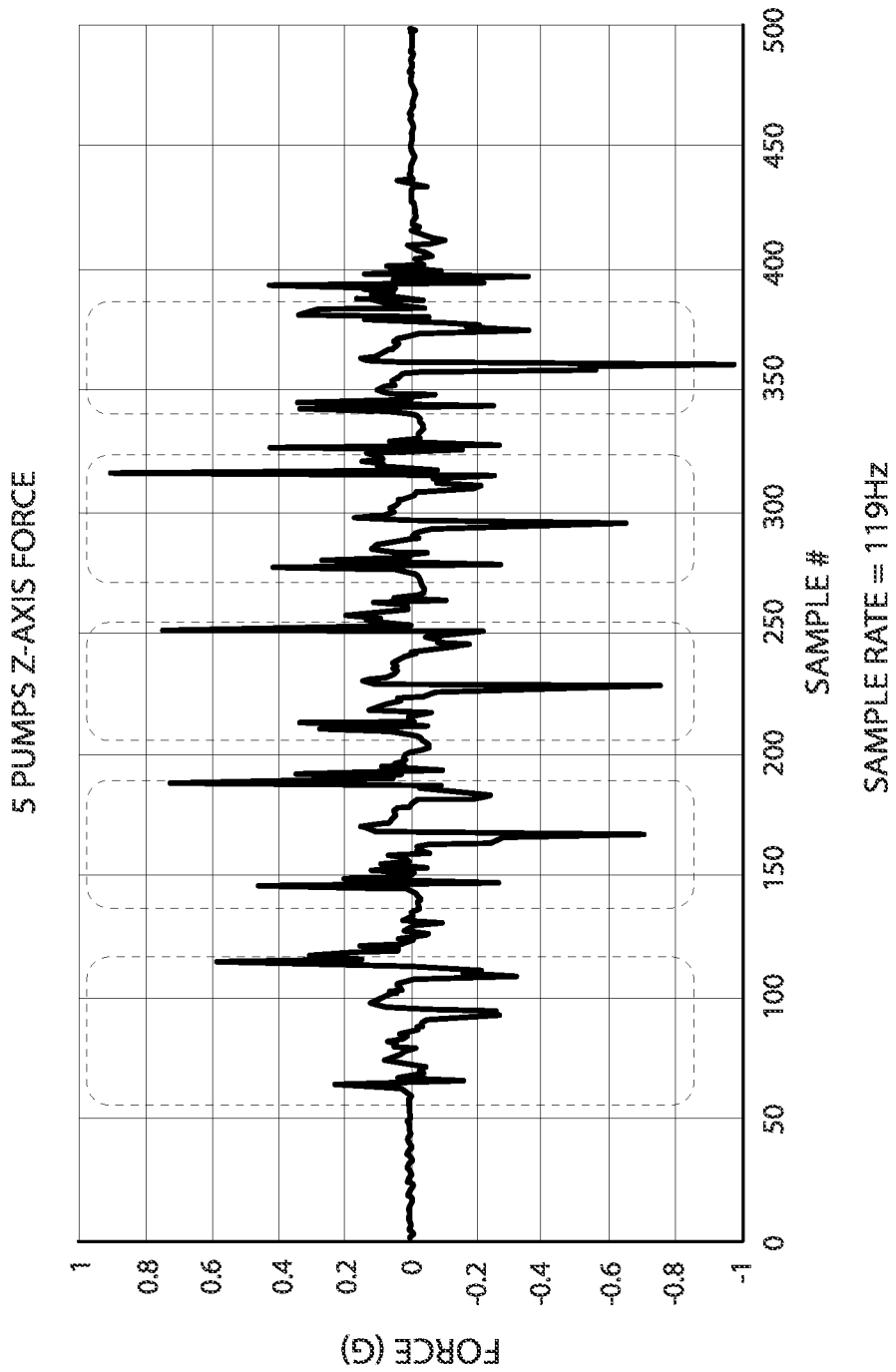
FIG. 26 illustrates raw accelerometer data for multiple pumps.
Figure 27:
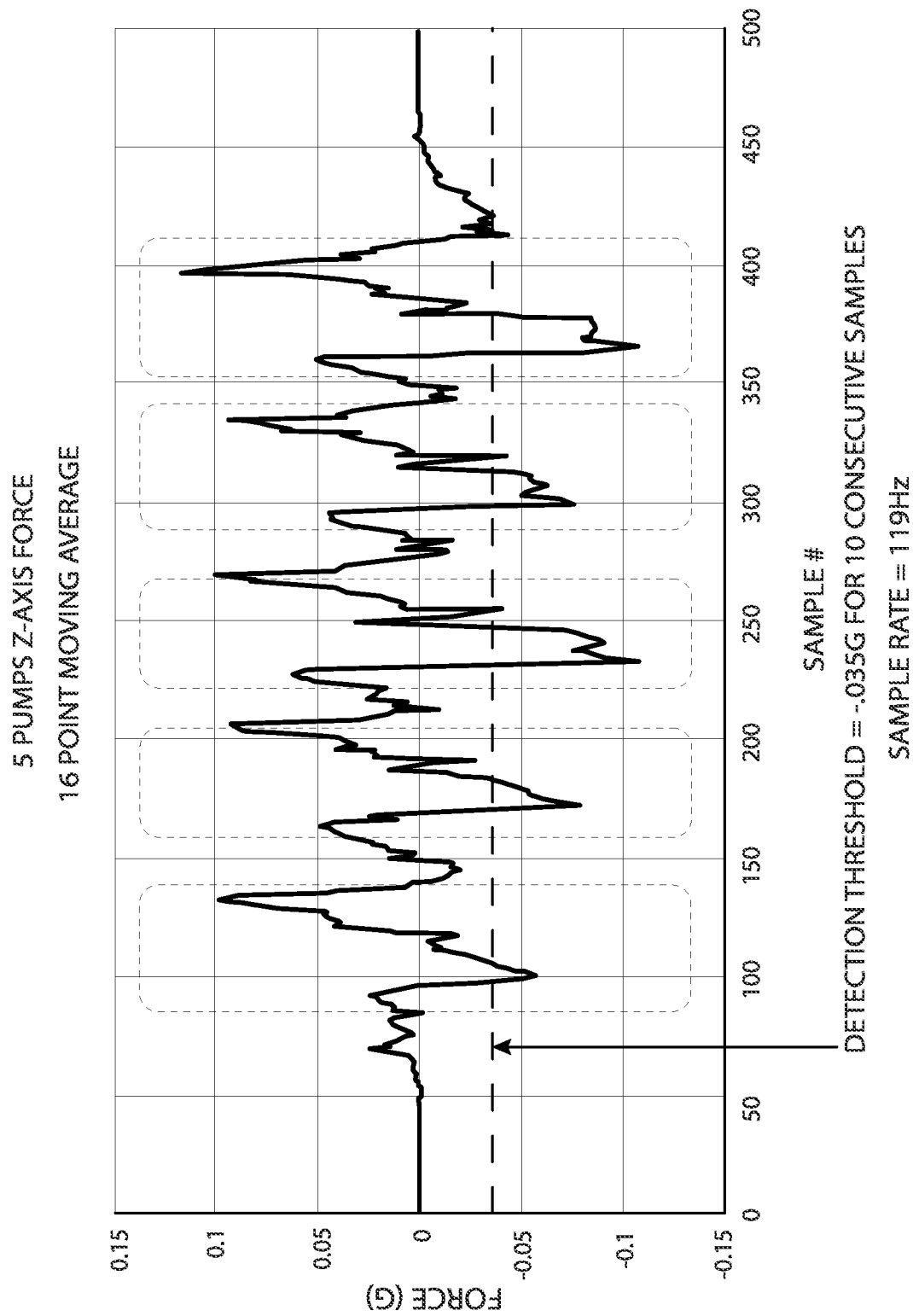
FIG. 27 illustrates filtered accelerometer data for multiple pumps.

Exemplary raw and processed data associated collected from an accelerometer and provided to the controller during a pump event is represented in FIGS. 26 and 27. FIG. 26 shows the raw information provided by the accelerometer for a series of five dispense pumps in a short period of time. It can be difficult to discern the individual pumps from other forces or noise sources in the system. Accordingly, the controller can be utilized to perform digital signal processing. For example, FIG. 27 illustrates a 16-sample moving average of the raw data of FIG. 26, which results in a cleaner waveform with discrete pump waveforms. By monitoring the filtered accelerometer data, the controller can determine a pump dispense occurred by checking the acceleration value exceeds a threshold, for example in the depicted embodiment a threshold of −0.035 g for ten consecutive samples was used to identify a pump and increment the pump counter.

The controller actively monitors and increments a counter for both the number of capacitive touches on the top of the pump as well as the number of accelerometer readings that indicate a pump has occurred. The controller will reset a second timer that will timeout 10 seconds after the last touch or pump was detected. After this timeout occurs, the controller can log a time stamp, duration of pumping interaction, number of touches, and number of pumps to the memory located within the product interaction monitor.

Once the pump event is complete the controller can log the event in memory and/or transmit the event to a third party device. The log of the event can include raw sensor data, processed results, or a combination thereof. For example, the raw sensor data, filtered sensor data, and a result such as an estimate of the amount of product dispensed, for example an estimate determined by multiplying each pump (e.g., −0.035 g for 10 consecutive samples), by a predetermined amount of product. Alternatively, the estimate of amount of product dispensed may be more accurately calculated by determining the travel distance of the pump and a correlation factor between pump travel distance and dispensed product. The correlation factor can vary depending a variety of different characteristics such as the characteristic of the fluid being dispensed and the construction of the pump. Just as discussed in connection with the twist-off embodiment, the product interaction monitor, including the controller, power source, and sensors, can be installed hidden from view of a human user and therefore this information can be collected, logged, and communicated to a third party device stealthily without the user's knowledge, which can increase effectiveness of clinical trials.

Directional terms, such as "vertical," "horizontal," "top," "bottom," "upper," "lower," "inner," "inwardly," "outer" and "outwardly," are used to assist in describing the invention based on the orientation of the embodiments shown in the illustrations. The use of directional terms should not be interpreted to limit the invention to any specific orientation(s).

The above description is that of current embodiments of the invention. Various alterations and changes can be made without departing from the spirit and broader aspects of the invention as defined in the appended claims, which are to be interpreted in accordance with the principles of patent law including the doctrine of equivalents. This disclosure is presented for illustrative purposes and should not be interpreted as an exhaustive description of all embodiments of the invention or to limit the scope of the claims to the specific elements illustrated or described in connection with these embodiments. For example, and without limitation, any individual element(s) of the described invention may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Further, the disclosed embodiments include a plurality of features that are described in concert and that might cooperatively provide a collection of benefits. The present invention is not limited to only those embodiments that include all of these features or that provide all of the stated benefits, except to the extent otherwise expressly set forth in the issued claims. Any reference to claim elements in the singular, for example, using the articles "a," "an," "the" or "said," is not to be construed as limiting the element to the singular.

The embodiments of the invention in which an exclusive property or privilege is claimed are defined as follows:

1. A product interaction monitor for a dispenser, the product interaction monitor comprising:
    a product interaction monitor housing configured for installation onto the dispenser, wherein said product interaction monitor housing and components mounted to said product interaction monitor housing, when installed on the dispenser, are hidden from external view of the dispenser;
    a power source mounted to said product interaction monitor housing;
    a sensor system mounted to said product interaction monitor housing, said sensor system including an accelerometer having low power and normal modes;
    a memory for storing said product interaction monitor data;
    a controller mounted to said product interaction monitor housing, said controller configured to:
        collect product interaction monitor data from said accelerometer of said sensor system;
        determine a plurality of different events associated with the dispenser based on different combinations of thresholds, samples, and timing sequences from said accelerometer of said sensor system;
        detect a wake-up event based on sensor output from said accelerometer configured in low power mode;
        monitor output of said accelerometer configured in normal mode for angular velocity in three axes;
        increment a movement counter associated with the dispenser in response to accelerometer output above one of a plurality of different axis angular velocity thresholds during a wakeup timeout period;
        reset the wakeup timeout period in response to the movement counter being incremented during said wakeup timeout period;
        log a user interaction event in said memory in response to said wakeup timeout period expiring without being reset; and
    a wireless transmitter configured to wirelessly transmit the user interaction event to a device external to the dispenser.

2. The product interaction monitor of claim 1 wherein said accelerometer is configured to detect a container upright condition and wherein the controller is configured to permit time of flight inventory measurements in response to detection of the container upright condition.

3. The product interaction monitor of claim 1 wherein said accelerometer is configured to detect a container tilted condition and wherein the controller is configured to restrict time of flight inventory measurements in response to the container tilted condition.

4. The product interaction monitor of claim 1 wherein said sensor system includes a capacitive touch sensor, wherein said controller is configured to determine a plurality of different events associated with the dispenser based on different combinations of thresholds, samples, and timing sequences from said accelerometer and said capacitive touch sensor.

5. The product interaction monitor of claim 1 wherein the product interaction monitor housing is configured for installation within a fluid pump dispenser cap of a fluid pump dispenser.

6. The product interaction monitor of claim 1 wherein the product interaction monitor housing is configured for installation within a flip-top dispenser cap of a dispenser.

7. The product interaction monitor of claim 1 wherein the product interaction monitor housing is configured for installation within a twist off cap of a dispenser.

8. A product interaction monitor for a dispenser, the product interaction monitor comprising:
    a product interaction monitor housing configured for installation onto the dispenser, wherein the product interaction monitor housing and components mounted to the product interaction monitor housing, when installed on the dispenser, are hidden from external view of the dispenser;
    a power source mounted to the product interaction monitor housing;
    a sensor system mounted to the product interaction monitor housing, the sensor system including an accelerometer and a capacitive sensor;
    a controller configured to collect product interaction monitor compliance data from said accelerometer and said capacitive sensor of said sensor system and configured to determine a plurality of different events associated with the dispenser based on different combinations of thresholds, samples, and timing sequences from said accelerometer and said capacitive sensor of said sensor system, the controller mounted to the product interaction monitor housing and including a memory for storing the product interaction monitor data;
    wherein said controller is configured to detect a wake-up touch event in response to a capacitive sensor output above a predetermined wake-up capacitance threshold;
    wherein said controller is configured to wake up said accelerometer in response to the wake-up touch event, configured to monitor said accelerometer for a movement count event associated with the dispenser based on receiving accelerometer output above a movement count threshold angular velocity within a wakeup timeout period, and configured to monitor said capacitive sensor for a touch count event associated with the dispenser based on receiving capacitive sensor output above a pre-defined touch count threshold capacitance within the wakeup timeout period;
    wherein said controller is configured to reset the wakeup timeout period in response to the movement count event and wherein the controller is configured to reset the wakeup timeout period in response to the touch count event;
    wherein in response to the wakeup timeout period expiring without being reset, said controller is configured to log a user interaction event in the memory; and
    a wireless transmitter configured to wirelessly transmit user interaction events to a device external to the dispenser.

9. The product interaction monitor of claim 8 wherein said accelerometer is configured to detect a container upright condition and wherein the controller is configured to permit time of flight inventory measurements in response to detection of the container upright condition.

10. The product interaction monitor of claim 8 wherein said accelerometer is configured to detect a container tilted condition and wherein the controller is configured to restrict time of flight inventory measurements in response to the container tilted condition.

11. The product interaction monitor of claim 8 wherein the product interaction monitor housing is configured for installation within a fluid pump dispenser cap of a fluid pump dispenser.

12. The product interaction monitor of claim 8 wherein the product interaction monitor housing is configured for installation within a flip-top dispenser cap of a dispenser.

13. The product interaction monitor of claim 8 wherein the product interaction monitor housing is configured for installation within a twist off cap of a dispenser.

14. The product interaction monitor of claim 8 wherein said accelerometer is configured to detect a container upright condition and wherein the controller is configured to permit time of flight inventory measurements in response to detection of the container upright condition.

15. A smart fluid dispensing pump cap for a fluid dispenser, the smart fluid dispensing pump cap comprising:
    a dispensing pump cap housing configured to mount to a neck of the fluid container;
    a dispensing pump configured to travel in two directions along one axis to pump fluid out of the fluid container;
    a power source;
    a sensor system including an accelerometer and a capacitive sensor, the capacitive sensor configured to change capacitance in response to touch of an external surface of the smart fluid dispensing pump housing, the accelerometer configured to measure positive and negative acceleration as the pump travels in two directions along the one axis to pump fluid out of the fluid container;
    a memory for storing dispensing pump interaction data;
    a controller configured to collect dispensing pump interaction data from said accelerometer and said capacitive sensor of said sensor system and configured to determine a plurality of different events associated with the fluid dispenser based on different combinations of thresholds, samples, and timing sequences from said accelerometer and said capacitive sensor of said sensor system;
    wherein said controller is configured to detect a wake-up touch event in response to a capacitive sensor output above a predetermined wake-up capacitance threshold;
    wherein said controller is configured to wake up said accelerometer in response to the wake-up touch event, configured to monitor said accelerometer for a movement count event associated with said dispensing pump based on accelerator output above a movement count threshold angular velocity within a wakeup timeout period, and configured to monitor said capacitive sensor for a touch count event associated with said dispensing pump based on capacitive sensor output above a pre-defined touch count threshold capacitance within said wakeup timeout period;

wherein said controller is configured to reset said wakeup timeout period in response to said movement count event and wherein said controller is configured to reset said wakeup timeout period in response to said touch count event;

wherein in response to said wakeup timeout period expiring without being reset, said controller is configured to log a user interaction event in said memory; and a wireless transmitter configured to wirelessly transmit a user interaction event to a device external to said smart fluid dispensing pump cap.

16. The smart fluid dispensing pump cap of claim 15 wherein said accelerometer is configured to detect the fluid dispenser is in an upright condition and wherein the controller is configured to permit time of flight inventory measurements in response to detection of the upright condition of the fluid dispenser.

17. The smart fluid dispensing pump cap of claim 15 wherein said accelerometer is configured to detect the fluid dispenser is in a tilted condition and wherein the controller is configured to restrict time of flight inventory measurements in response to detection of the tilted condition of the fluid dispenser.

18. The smart fluid dispensing pump cap of claim 15 wherein the controller is configured to perform digital signal processing to discern discrete pump waveforms from the accelerometer measurements.

19. The smart fluid dispensing pump cap of claim 15 wherein the controller estimates an amount of product dispensed by application of a correlation factor between pump travel distance and dispensed product.

20. The smart fluid dispensing pump cap of claim 15 wherein when the smart fluid dispensing pump cap is installed on a fluid dispenser, the controller, sensing system, and power source are hidden from external view of the dispenser.

* * * * *